US009511199B2

(12) United States Patent
Patel et al.

(10) Patent No.: US 9,511,199 B2
(45) Date of Patent: *Dec. 6, 2016

(54) PORE STRUCTURES FOR REDUCED PRESSURE AEROSOLIZATION

(71) Applicant: ARADIGM CORPORATION, Hayward, CA (US)

(72) Inventors: Rajesh S. Patel, Fremont, CA (US); Sudarsan Srinivasan, Fremont, CA (US)

(73) Assignee: Aradigm Corporation, Hayward, CA (US)

( * ) Notice: Subject to any disclaimer, the term of this patent is extended or adjusted under 35 U.S.C. 154(b) by 284 days.

This patent is subject to a terminal disclaimer.

(21) Appl. No.: 14/157,134

(22) Filed: Jan. 16, 2014

(65) Prior Publication Data
US 2014/0174439 A1 Jun. 26, 2014

Related U.S. Application Data

(60) Continuation of application No. 13/088,572, filed on Apr. 18, 2011, now abandoned, which is a division of application No. 11/872,483, filed on Oct. 15, 2007, now abandoned, which is a continuation of application (Continued)

(51) Int. Cl.
*B05B 1/08* (2006.01)
*A61M 15/00* (2006.01)

(52) U.S. Cl.
CPC ....... *A61M 15/009* (2013.01); *A61M 15/0031* (2014.02); *A61M 15/0043* (2014.02);
(Continued)

(58) Field of Classification Search
CPC .................. A61M 15/0065; A61M 15/0085; A61M 15/0021; B05B 17/0646; B05B 17/0607; B05B 7/08

USPC ........................... 239/102.1, 102.2, 548, 596
See application file for complete search history.

(56) References Cited

U.S. PATENT DOCUMENTS 4,702,418 A * 10/1987 Carter ...................... A61L 9/14
239/101
4,794,615 A  12/1988 Berger et al.
(Continued)

FOREIGN PATENT DOCUMENTS

CA      2255918      11/1992
CA      2203257      5/1996
(Continued)

OTHER PUBLICATIONS

Srinivasan, et al., "Self-developing photoetching of poly(ethylene terephthalate) films by far-ultraviolet excimer laser radiation", Applied Physics Letters, 1982, 41(6):576-578.

*Primary Examiner* — Davis Hwu
(74) *Attorney, Agent, or Firm* — Paula A. Borden; Bozicevic, Field & Francis LLP

(57) ABSTRACT

A nozzle comprising a thin, flexible substantially planar polymeric film having a plurality of pores with structures allowing for generation of an aerosol at reduced extrusion pressure is disclosed. The pores can comprise at least two sections, or steps, in which the thickness of the membrane is reduced in stepwise fashion, or the pores can be tapered. Nozzles formed comprising pores having such structures permit aerosol generation at lower extrusion pressures, thereby allowing for decreased weight of aerosolization devices, increased efficiency, increased portability and increased battery life. The pore structures also allow for the use of thicker, more easily processed polymeric films in manufacturing while having a thinner, more efficient aerosolization area. The use of decreased extrusion pressures also results in increased uniformity in aerosol generation and improved reliability of other components.

15 Claims, 12 Drawing Sheets

Related U.S. Application Data

No. 10/808,046, filed on Mar. 23, 2004, now Pat. No. 7,316,360, which is a continuation of application No. 10/095,898, filed on Mar. 11, 2002, now Pat. No. 6,732,954, which is a continuation of application No. 09/432,890, filed on Nov. 2, 1999, now Pat. No. 6,354,516, and a continuation of application No. 09/192,833, filed on Nov. 16, 1998, now Pat. No. 6,070,575.

(60) Provisional application No. 60/154,198, filed on Sep. 15, 1999.

(52) U.S. Cl.
CPC ..... *A61M15/0045* (2013.01); *A61M 15/0051* (2014.02); *A61M 15/0055* (2014.02); *Y10T 29/49826* (2015.01)

(56) References Cited

U.S. PATENT DOCUMENTS

| | | |
|---|---|---|
| 4,894,115 A | 1/1990 | Eichelberger et al. |
| 5,181,212 A | 1/1993 | Moberg |
| 5,387,211 A | 2/1995 | Saadatmanesh et al. |
| 5,404,871 A | 4/1995 | Goodman et al. |
| 5,417,897 A | 5/1995 | Asakawa et al. |
| 5,450,336 A | 9/1995 | Rubsamen et al. |
| 5,497,763 A | 3/1996 | Lloyd et al. |
| 5,497,944 A | 3/1996 | Weston |
| 5,544,646 A | 8/1996 | Lloyd et al. |
| 5,660,166 A | 8/1997 | Lloyd et al. |
| 5,709,202 A | 1/1998 | Lloyd et al. |
| 5,718,222 A | 2/1998 | Lloyd et al. |
| 5,753,014 A | 5/1998 | Van Rijn |
| 5,811,019 A | 9/1998 | Nakayama et al. |
| 5,823,178 A | 10/1998 | Lloyd et al. |
| 5,829,435 A | 11/1998 | Rubsamen et al. |
| 5,855,564 A | 1/1999 | Ruskewicz |
| 5,906,202 A | 5/1999 | Schuster et al. |
| 6,008,468 A | 12/1999 | Tanaka et al. |
| 6,070,575 A | 6/2000 | Gonda et al. |
| 6,230,706 B1 | 5/2001 | Gonda et al. |
| 6,295,986 B1 | 10/2001 | Patel et al. |
| 6,354,516 B1 | 3/2002 | Patel et al. |
| 6,551,542 B1 | 4/2003 | Patel et al. |
| 6,689,986 B2 | 2/2004 | Patel et al. |
| 6,855,909 B2 | 2/2005 | Patel et al. |
| 7,316,360 B2 | 1/2008 | Patel et al. |

FOREIGN PATENT DOCUMENTS

| | | |
|---|---|---|
| JP | 08-299862 | 11/1996 |
| JP | 10-506037 | 6/1998 |
| WO | WO 94/25259 | 11/1994 |
| WO | WO 96/09846 | 4/1996 |
| WO | WO 96/13292 | 5/1996 |

\* cited by examiner

FIG. 2
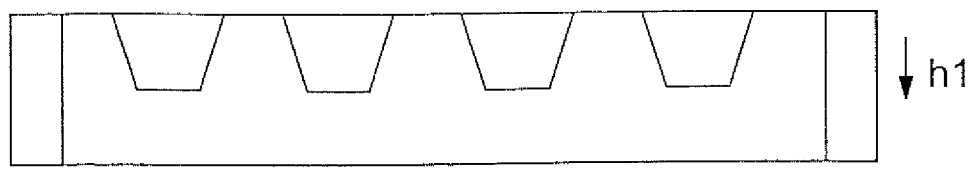
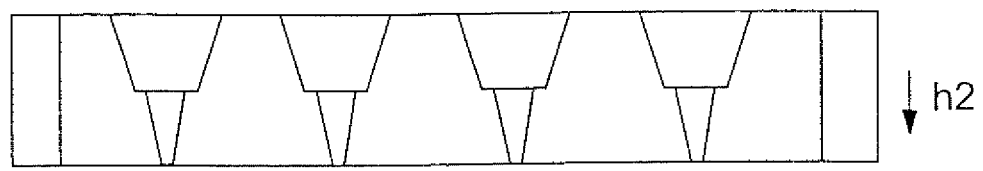

PORE STRUCTURES FOR REDUCED PRESSURE AEROSOLIZATION

CROSS-REFERENCE

This application is a continuation of U.S. patent application Ser. No. 13/088,572, filed Apr. 18, 2011, which is a divisional of U.S. patent application Ser. No. 11/872,483, filed Oct. 15, 2007, which is a continuation application of U.S. patent application Ser. No. 10/808,046, filed Mar. 23, 2004, now U.S. Pat. No. 7,316,360, which is a continuation of U.S. patent application Ser. No. 10/095,898, filed Mar. 11, 2002, now U.S. Pat. No. 6,732,954, which is a continuation of U.S. patent application Ser. No. 09/432,890, filed Nov. 2, 1999, now U.S. Pat. No. 6,354,516, which claims the benefit of U.S. Provisional Patent Application Ser. No. 60/154,198, filed Sep. 15, 1999 and which is a continuation of U.S. patent application Ser. No. 09/192,833, filed Nov. 16, 1998, now U.S. Pat. No. 6,050,575, each of which applications is incorporated herein by reference in its entirety.

FIELD OF THE INVENTION

This invention relates generally to devices and methods for aerosolizing formulations. More specifically, this invention relates to an aerosolization nozzle comprising a membrane having pore structures for reduced pressure aerosolization.

BACKGROUND OF THE INVENTION

Aerosolization is a desirable means for the delivery of therapeutic or diagnostic agents. Aerosol delivery avoids the problems associated with other delivery methods such as oral administration or injection. Injections are painful, present a risk of infection to the health-care provider from an inadvertent needle-stick, and create hazardous waste from the needle and syringe. Additionally, repeated injections can result in scarring. Oral administration must overcome several obstacles to the delivery of agents, including the acidic environment of the stomach, the ability of the agent to pass through the of the intestinal wall, and first-pass metabolism of the agent by the liver. Aerosol delivery, on the other hand, allows the direct delivery of agents to areas such as the nasal tract, the respiratory tract, or the eye, as well as systemic delivery into the circulation by administration to the respiratory tract and uptake into the circulation.

Currently available methods of generating and delivering aerosols to the nasal and respiratory tract include metered-dose inhalers, dry powder inhalers and nebulizers. Available methods of delivering agents to the eye include ointments and eye drops.

Co-owned U.S. Pat. Nos. 5,544,646; 5,718,222; 5,660,166; 5,823,178; 5,709,202; and 5,906,202 describe devices and methods useful in the generation of aerosols suitable for drug delivery. A drug formulation is forcibly applied to one side of a pore-containing membrane so as to produce an aerosol on the exit side of the membrane. Aerosols containing particles with a more uniform size distribution can be generated using such devices and methods, and can be delivered to particular locations within the respiratory tract.

However, the high pressures which must be used to generate acceptable aerosols present significant limitations on aerosolization devices. Sufficient power must be provided by the devices to generate the desired pressure. Larger power sources increase the weight of these devices, and thereby decrease the mobility of patients. In portable devices, battery life is also decreased by higher power needs. Additionally, higher pressures increase the required pressure tolerances of other system components. Elevated pressures may also lead to variability in aerosol quality.

SUMMARY OF THE INVENTION

The present invention provides aerosolization nozzles for use in aerosolization devices for delivering a formulation, which may contain a drug(s) and/or diagnostic agent(s), to an individual. Aerosolization nozzles of the present invention comprise a membrane having pore structures that are particularly well suited for aerosolization at reduced extrusion pressures. By decreasing the pressure which must be supplied to generate a uniform aerosol, such nozzles allow for decreased weight of the delivery devices and increased patient mobility. Battery life is thereby increased, leading to further increases in patient mobility. Additionally, at lower pressures the required tolerances of other system components is reduced. Reduced pressure during aerosolization may also result in increased aerosol uniformity and improved reliability of such aerosolization devices.

The membrane has an entrance side to which formulation is applied under pressure, and an exit side, from which aerosol is extruded, and a nozzle area, which has a plurality of pores penetrating the thickness of the membrane. The membrane is preferably flexible. Each pore has an entrance diameter (or cross-sectional area) and an exit diameter (or cross-sectional area). The exit aperture of the pores in the nozzle is of a size sufficient to generate an aerosolized particle of the desired size.

The pore structures of the present invention have an increased entrance diameter to exit diameter ratio when compared to those in previously described aerosolization nozzles. Generally, the ratio is at least 10:1. In some embodiments, this ratio is 15:1. In other embodiments, this ratio is 25:1 or greater.

These specialized pore structures ("reduced-pressure aerosolization pores") confer a major advantage when formed in aerosolization membranes, in that the reduced pressure required to force a flowable formulation through a nozzle comprising these specialized pores such that an aerosol is generated is significantly reduced. Thus, in some of these embodiments, the pressure required to force a formulation through the pores, such that an aerosol is generated in an acceptably short period of time, is less than about 500 pounds per square inch (psi), generally less than about 400 psi, usually less than about 300 psi, down to about 200 psi or less.

The cross-sectional profile of the pores can be discontinuous (i.e., multi-step), or continuous, (i.e., tapered). When the cross-sectional profile of a pore is discontinuous, the diameter and/or cross-sectional area of a given pore step is reduced in a step-wise fashion, relative to the preceding pore step. When the cross-sectional profile of a pore is tapered, the diameter from the entrance side to the exit side decreases in a substantially continuous fashion, i.e., there is a gradual diminution of diameter of the pore from the entrance side to the exit side.

One aspect of the invention is a nozzle for aerosolizing a formulation for respiratory delivery, said nozzle comprising a membrane having about 10 to about 1,000 reduced-aerosolization pressure pores per square millimeter, said pores having an average relaxed exit aperture diameter of from about 0.5 to about 5 μm and are spaced at a distance of from about 30 to about 70 μm apart from each other.

In yet another aspect of the invention, a nozzle is provided wherein the pores are incompletely formed so that, upon administration of pressure to the entrance side of the film, the exit aperture is formed by bursting outward the exit side of the pores, thereby forming an elevated area preventing liquid intrusion into the exit aperture.

In a further aspect of the invention, a strip containing multiple nozzle areas comprising reduced-pressure aerosolization pores is provided.

In a further aspect of the invention, a container is provided which comprises at least one wall which is reversible collapsible upon application of a force, and which includes at least one opening leading to an open channel, at the end of which is a nozzle of the invention. The container can contain a flowable formulation which, upon application of a force to the collapsible wall, is forced through the channel and the nozzle, whereupon an aerosol is generated. The invention further provides a package comprising a plurality of such containers.

In another aspect, an aerosolization device comprising a nozzle of the invention is provided. In preferred embodiments, the device is provided as a disposable package.

These and other objects, aspects, features, and advantages will become apparent to those skilled in the art upon reading the disclosure in combination with the figures forming a part hereof.

BRIEF DESCRIPTION OF THE DRAWINGS

FIG. 2 is a schematic drawing of a two-step pore formed via multi-step laser ablation.

DETAILED DESCRIPTION OF THE INVENTION

Figure 1:
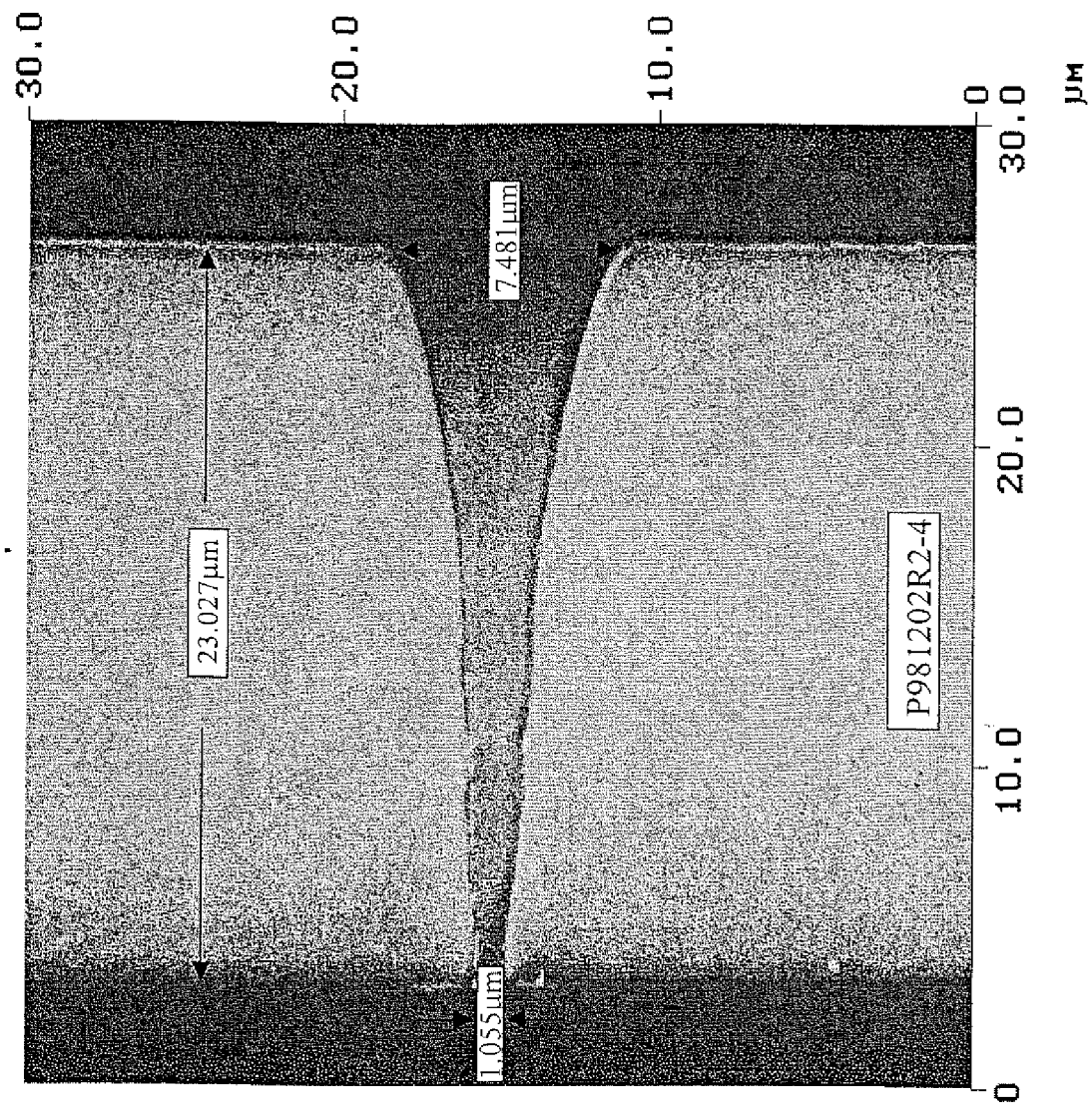
FIG. 1 is a scanning electron micrograph of a pore formed via single-step laser ablation for a "standard" nozzle. Dimensions are given in micrometers.

The invention provides improved nozzles comprising a membrane having pores of small, uniform size for aerosolizing any type of drug or diagnostic agent that permits the generation of uniform aerosols at reduced pressures as compared with previous nozzles. The membranes have an entrance side to which formulation is applied under pressure, and an exit side, from which the aerosol is released. The small exit aperture sizes required to generate aerosolized particles suitable for delivery, e.g., to the lung, also require high extrusion pressures to force a liquid formulation through the pores in the nozzle. In previous aerosolization nozzles, the required pressure to extrude a liquid formulation through a nozzle area having pores with an entrance diameter to exit diameter ratio of about 5-6 were in the range of about 650 to about 750 psi. The pressure required for aerosolization from a pore having a given exit aperture size decreases with increasing entrance aperture size. Thus, increasing the entrance aperture size relative to the exit aperture size (other factors being equal) reduces the pressure needed for aerosolization and thereby improves system performance.

In the present invention, the pores of the membrane have structures that allow extrusion of a flowable formulation at reduced pressures, usually less than about 500 psi, generally in the range of about 200 to about 400 psi or less, wherein an aerosol is generated. This is achieved by generating pores having entrance diameter to exit diameter ratios about 10:1, about 25:1, or greater.

The pores can have a discontinuous, step-wise, cross-sectional profile, or a continuous, tapered, cross-sectional profile. The pores are formed so as to have a relatively high entrance aperture size relative to exit aperture size. Nozzles formed in this way allow for improved handling of the nozzle material during manufacturing and increase the reliability of aerosolization devices incorporating them by operating at lower pressures. The present invention provides aerosolization nozzles comprising these membranes, as well as methods of creating such pore structures.

A method of generating an aerosol from such nozzles is also provided. The devices used in conjunction with the present invention can be hand-held, self-contained, highly portable devices which provide a convenient means of delivering drugs or diagnostic agents to a patient. Because of decreased power needs for aerosolization, the devices can be lighter and have increased battery life, leading to improved patient mobility.

In general, an aerosol for respiratory or ocular delivery is generated from a drug or diagnostic agent formulation, preferably a flowable formulation, more preferably a liquid, flowable formulation. The drug or diagnostic agent formulation can be contained within a multidose container or within a container portion of a disposable package, where the container of the disposable package has at least one surface that is collapsible. The aerosol is generated by applying pressure of 500 psi or less, preferably 400 psi or less, more preferably 300 psi or less, down to about 200 psi, to the collapsible container surface, thereby forcing the contents of the container through a nozzle comprised of a porous membrane, such that an aerosol is generated. The porous membrane may be rigid or flexible. Preferably the porous membrane is flexible so that upon application of the pressure required to aerosol the formulation, the nozzle's porous membrane becomes convex in shape, thus delivering the aerosolized drug or diagnostic agent into the flow path of the delivery device in a region beyond the flow boundary layer.

The amount of pressure needed to create an aerosol is determined by several factors, including: (1) the ratio of the size of the entrance aperture to the exit aperture; (2) the size of the exit apertures; (3) the pore density, i.e., the number of pores per unit area of the membrane; (4) the amount of liquid being aerosolized; (5) the period of time for aerosolization; (6) the viscosity of the liquid being aerosolized; and (7) the pressure at the exit opening. Other factors such as temperature, atmospheric pressure, and humidity can also affect the pressure needed to create an aerosol. Unless stated otherwise, factors other than the ratio of entrance to exit diameter will remain the same and be standard.

The formulations for use in the present invention can include preservatives or bacteriostatic type compounds. However, the formulation preferably comprises a pharmaceutically active drug (or a diagnostic agent) and pharmaceutically acceptable carrier. The formulation can be primarily or essentially composed of the drug or diagnostic agent (i.e., without carrier) if the drug or diagnostic agent is freely flowable and can be aerosolized. Useful formulations can comprise formulations currently approved for use with nebulizers or for injections.

Further, the dispensing device of the present invention, which can be used to dispense a drug or diagnostic agent formulation according to the method of the invention, preferably includes electronic and/or mechanical components which eliminate direct user actuation of drug release. More specifically, where the device is used in respiratory therapy, the device preferably includes a means for measuring inspiratory flow rate and inspiratory volume and sending an electrical signal as a result of the simultaneous measurement of both (so that drug or diagnostic agent can be released at a preprogrammed optimal point) and also preferably includes a microprocessor which is programmed to receive, process, analyze and store the electrical signal of the means for measuring flow and upon receipt of signal values within appropriate limits sending an actuation signal to the mechanical means which causes drug (or diagnostic agent) to be extruded from the pores of the nozzle's porous membrane. Thus, since preferred embodiments of the devices used in connection with the present invention include a means of analyzing breath flow and a microprocessor capable of making calculations based the inhalation profile, the present invention can provide a means for repeatedly (1) dispensing and (2) delivering the same amount of the drug or diagnostic agent to a patient at each dosing event.

Before the present nozzles (comprising membranes with reduced-pressure aerosolization pores), devices, containers, formulations and methods used in connection with such are described, it is to be understood that this invention is not limited to the particular methodology, devices, containers and formulations described, as such methods, devices, containers and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "a pore" includes one or more pores, and reference to "the method of treatment" and to "the method of diagnosis" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited.

The publications discussed herein, supra and infra, are provided solely for their disclosure prior to the filing date of the present application. Nothing herein is to be construed as an admission that the invention is not entitled to antedate such disclosure by virtue of prior invention.

DEFINITIONS

The term "porous membrane" shall be interpreted to mean a membrane of material having any given outer parameter shape, but preferably having a convex shape, or being capable of flexing into a convex shape, wherein the membrane has a plurality of pores therein, which openings may be placed in a regular or irregular pattern. The pores of the membrane have an entrance diameter larger than the exit diameter, and the ratio of entrance:exit diameter is 5 or more to 1, preferably 10:1 or greater, more preferably 15:1 or greater, more preferably 25:1 or greater. Preferably, the membrane has pores which have an unflexed diameter of their exit aperture in the range of 0.25 micron to 6 microns and a pore density in the range of 1 to 1,000 pores per square millimeter for respiratory delivery. For ocular delivery, the pores have an unflexed diameter of their exit aperture in the range of 0.5 microns to 50 microns, generally 1.0 to 25 microns, and a similar pore density. The porous membrane has a porosity of about 0.0005% to 0.2%, preferably about 0.01% to 0.1%. In one embodiment, the porous membrane comprises a single row of pores on, e.g., a large piece of membrane material. The pores may be planar with respect to the surface of the porous membrane material, or may have a conical configuration.

For purposes of the present invention, a porous membrane has an entrance side, to which formulation is applied under pressure, and an exit side, from which the aerosol is released. The membrane also has a nozzle area, through which a plurality of pores passes. The pores pass substantially perpendicularly through the thickness of the membrane, from the entrance side to the exit side. Each pore has an entrance diameter (or cross-sectional area) and an exit diameter (or cross-sectional area).

A "tapered pore", as used herein, refers to a pore whose diameter and/or cross-sectional area decreases in a substantially continuous fashion from the entrance side to the exit side of the membrane.

A "stepped pore", or "multistep pore", as used herein, intends a pore whose diameter and/or cross-sectional area decreases in a stepwise, discontinuous fashion from the entrance side to the exit side of the porous membrane through which it passes, in contradistinction to the substantially continuous, linear decrease in diameter characteristic of a cone, or the uniform diameter of a cylinder. A "stepped pore" refers to a pore which has at least one abrupt change in pore size, but that abrupt change may be followed by a second smooth or continuous change in size, i.e., a pore step may be substantially cylindrical or cone-shaped. A "stepped pore" is a pore having a discontinuous cross-sectional profile, an example of which is shown schematically in FIG. 2. The term "pore step", as used herein, refers to a segment of a multistep pore. A pore step passes through a portion, having a height h, of the membrane material forming the nozzle, where h is less than the thickness of the membrane. The term "multistep pore" intends pores comprising two or more of such steps. Each step is progressively, and discontinuously, reduced in diameter relative to the preceding step, going from the entrance to exit side of the membrane, ultimately resulting in an exit aperture size capable of producing aerosol particles of the desired size. Said another way, the diameter of the pore decreases abruptly from one step to the next, going from the entrance side of the membrane to the exit side of the membrane. A given multistep pore is said to have a pore entrance aperture, i.e., the aperture on the entrance side of the membrane, and a pore exit aperture, i.e., the aperture on the exit side of the membrane. Similarly, a given pore step is said to have a pore step entrance aperture and a pore step exit aperture. Each aperture has a size. If a given aperture is roughly circular, then the size can be described as the diameter. If a given aperture is irregularly shaped, or otherwise non-circular, then the size can be described as the cross-sectional area at the aperture. The position of a given pore step relative to another pore step can be expressed in terms of proximity to the entrance or exit side of the membrane. Thus, for example, the entrance aperture size of a given pore step can be described in relation to the exit aperture size of the preceding "entrance proximal" pore step. The step of the pore immediately adjacent to the exit side of the membrane from which the aerosol is produced is referred to as the "through-step" or "exit-step."

As used herein, a "standard" nozzle is one that comprises "standard" pore structures, i.e., pore structures having an entrance aperture size to exit aperture size ratio less than 10:1. An example of a standard pore structure is shown in FIG. 1.

The term "porosity" is used herein to mean a percentage of an area of a surface area that is composed of open space, e.g., a pore, hole, channel or other opening, in a membrane, nozzle, filter or other material. The percent porosity is thus defined as the total area of open space divided by the area of the material, expressed as a percentage (multiplied by 100). High porosity (e.g., a porosity greater than 50%) is associated with high flow rates per unit area and low flow resistance. In general, the porosity of the nozzle is less than 10%, and can vary from $10^{-3}\%$ to 10%, while the porosity of the filter is at least 1%, and preferably it is at least 50% porous.

The terms "package" and "disposable package" are used interchangeably herein and shall be interpreted to mean a container or two or more containers linked together by an interconnecting means wherein each container preferably includes one or more channels which provide for fluid connection from the container to a nozzle comprised of a porous membrane, which nozzle is preferably not positioned directly over the container, and wherein each container includes at least one surface that is collapsible in a manner so as to allow the forced displacement of the contents of the container through a low resistance filter and out the nozzle (without rupturing the container) in a manner such that the contents are aerosolized. There are at least two major variations of the package, depending on whether the drug can be stably stored in a liquid form or must be stored dry and combined with liquid immediately prior to aerosolization.

The contents of each container preferably comprises a formulation, preferably a flowable formulation, more preferably a liquid, flowable formulation, which includes a pharmaceutically active drug or a diagnostic agent. If the drug or diagnostic agent is not liquid and of a sufficiently low viscosity to allow the drug to be aerosolized, the drug or diagnostic agent is dissolved or dispersed in an excipient carrier, preferably without any additional material such as preservatives that might affect the patient. When the contents must be stored in a dry state, the package further includes another container that holds the liquid and can be combined with the dry drug immediately prior to administration.

The term "container" is used herein to mean a receptacle for holding and/or storing a drug formulation. The container can be single-dose or multidose, and/or disposable or refillable.

The term "cassette" shall be interpreted to mean a container which holds, in a protective cover, a package or a plurality of packages which packages are interconnected to each other and held in the cassette in an organized manner, e.g., interfolding or wound. The cassette is connectable to a dispensing device, which dispensing device may include a power source, e.g., one or more batteries which provide power to the dispensing device.

The term "low resistance filter" shall be interpreted to mean a filter of material having any given outer parameter shape, and having a plurality of openings therein, which openings may be placed in a regular or irregular pattern. The openings in the filter can be of any shape, and are preferably substantially evenly distributed throughout the filter surface area. Preferably, the porosity of the low resistance filter is greater than 50%, preferably at least 60%, more preferably at least 70%. Preferably, the low resistance filter prevents passage of particles greater than about 0.5 microns in size (e.g., having a diameter greater than 0.5 microns). Where the filter openings are pores, the pores can have a diameter in the range of from about 0.25 micron to 6 microns for respiratory tract delivery, or from about 5 microns to 50 microns for ocular delivery. The filter has an opening density in the range of from about 10 to 20,000,000 openings per $mm^2$. Preferably the filter has holes of about 0.5 μm positioned about 0.5 μm apart at a density of $10^6$ holes per $mm^2$. Preferably, the ratio of the pore density of the porous membrane to the low resistance filter is in the range of about 1:1.5 to about 1:100,000; the ratio of the pore diameter of the pores of the porous membrane to the diameter of the openings of the low resistance filter is in the range of from about 1:0.95 to 1:0.1. Preferably, the flow resistance of the filter is the same as or lower than the flow resistance of the porous membrane used in conjunction with the filter. The filter is preferably comprised of a material having a density in the range of 0.25 to 3.0 $mg/cm^2$, more preferably 1.7 $mg/cm^2$, and a thickness of about 10 microns to about 500 microns, more preferably about 20 to 150 microns. The filter can be made of any material suitable for use in the invention, e.g., cellulose ester, mixed cellulose ester, modified polyvinylidene fluoride, polytetrafluoroethylene, bisphen polycarbonate, borosilicate glass, silver, polypropylene, polyester, polyimide, polyether, or any suitable polymeric material. The filter material includes materials such as polycarbonates and polyesters which may have the pores formed therein by any suitable method, including anisotropic etching or by etching through a thin film of metal or other suitable material, electron discharge machining, or laser micromachining. The filter preferably has sufficient structural integrity such that it is maintained intact (i.e., will not rupture) when subjected to force up to about 40 bar, preferably up to about 50 bar during extrusion of the formulation through the pores (of filter or membrane). The porosity of the low resistance filter is 5-85%, preferably 70%, while the porosity of the nozzle is $10^{-4}\%$-1%, preferably 0.001%-0.1%.

The term "flow resistance" shall be interpreted to mean the resistance associated with the passage of a liquid or aerosol through a porous material, e.g., through the porous membrane or the low resistance filter described herein. Flow resistance is affected by the size and density of pores in the porous material, the viscosity of a liquid passing through the material, and other factors well known in the art. In general, "low resistance" of the "low resistance filter" means that the flow resistance of the low resistance filter is substantially the same as or less than the flow resistance of the porous membrane used in conjunction with the low resistance filter.

The terms "drug", "active agent", "pharmaceutically active drug" and the like are used interchangeably herein to encompass compounds which are administered to a patient in order to obtain a desired pharmacological effect. The effect may be a local or topical effect in the eye or respiratory tract such as in the case of most respiratory or ophthalmic drugs or may be systemic as with analgesics, narcotics, hormones, hematopoietic drugs, various types of peptides including insulin, and hormones such as erythropoietin (EPO). Also included are polynucleotides encoding peptides, polypeptides, antisense polynucleotides, and ribozymes which have a desired pharmacological effect. Polynucleotides include, but are not limited to, polynucleotides encoding a DNase, a functional cystic fibrosis transmembrane conductance regulator (CFTR), and a peptide hormone. Combinations of one or more of the foregoing are also encompassed in the term "active agent". Other exemplary drugs are set forth in U.S. Pat. No. 5,419,315; U.S. Pat. No. 5,884,620; U.S. Pat. No. 5,888,477; U.S. Pat. No. 5,724,957; U.S. Pat. No. 5,558,085; U.S. Pat. No. 5,819,726; International Patent Application WO 96/13291; and International Patent Application WO 96/13290, all incorporated herein by reference to describe and disclose drugs.

The term "respiratory drug" shall be interpreted to mean any pharmaceutically effective compound used in the treatment of any respiratory disease and in particular the treatment of diseases such as asthma, bronchitis, emphysema and cystic fibrosis. Useful "respiratory drugs" include those which are listed within the Physician's Desk Reference (most recent edition). Such drugs include beta adrenergic agonists which include bronchodilators including albuterol, isoproterenol sulfate, metaproterenol sulfate, terbutaline sulfate, pirbuterol acetate, salmeterol xinotoate, formoteorol; steroids including corticosteroids used as an adjunct to beta agonist bronchodilators such as beclomethasone dipropionate, flunisolide, fluticasone, budesonide and triamcinolone acetonide; antibiotics including antifungal and antibacterial agents such as chloramphenicol, chlortetracycline, ciprofloxacin, framycetin, fusidic acid, gentamicin, neomycin, norfloxacin, ofloxacin, polymyxin, propamidine, tetracycline, tobramycin, quinolines, and the like; and also includes peptide nonadrenergic noncholinergic neurotransmitters and anticholinergics. Antiinflammatory drugs used in connection with the treatment of respiratory diseases include steroids such as beclomethasone dipropionate, triamcinolone acetonide, flunisolide and fluticasone. Other antiinflammatory drugs and antiasthmatics which include cromoglycates such as cromolyn sodium. Other respiratory drugs which would qualify as bronchodilators include anticholinergics including ipratropium bromide. Other useful respiratory drugs include leukotriene (LT) inhibitors, vasoactive intestinal peptide (VIP), tachykinin antagonists, bradykinin antagonists, endothelin antagonists, heparin furosemide, antiadhesion molecules, cytokine modulators, biologically active endonucleases, recombinant human (rh) DNase, $\alpha_1$ antitrypsin and antibiotics such as gentamicin, tobramycin, cephalosporins or penicillins, nucleic acids and gene vectors. The present invention is intended to encompass the free acids, free bases, salts, amines and various hydrate forms including semihydrate forms of such respiratory drugs and is particularly directed towards pharmaceutically acceptable formulations of such drugs which are formulated in combination with pharmaceutically acceptable excipient materials generally known to those skilled in the art—preferably without other additives such as preservatives. Preferred drug formulations do not include additional components such as preservatives which have a significant effect on the overall formulation. Thus preferred formulations consist essentially of pharmaceutically active drug and a pharmaceutically acceptable carrier (e.g., water and/or ethanol). However, if a drug is liquid without an excipient the formulation may consist essentially of the drug provided that it has a sufficiently low viscosity that it can be aerosolized using a dispenser of the present invention.

The term "ophthalmic drug" or "ophthalmic treatment fluid" refers to any pharmaceutically active compound used in the treatment of any ocular disease. Therapeutically useful compounds include, but are not limited to, (1) antiglaucoma compounds and/or compounds that decrease intraocular pressure such as β-adrenoceptor antagonists (e.g., cetamolol, betaxolol, levobunolol, metipranolol, timolol, etc.), mitotics (e.g., pilocarpine, carbachol, physostigmine, etc.), sympatomimetics (e.g., adrenaline, dipivefrine, etc.), carbonic anhydrase inhibitors (e.g., acetazolamide, dorzolamide, etc.), prostaglandins (e.g., PGF-2 alpha); (2) antimicrobial compounds including antibacterial and antifungal compounds (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines, etc.), (3) antiviral compounds (e.g., acyclovir, cidofovir, idoxuridine, interferons, etc.), (4) aldose reductase inhibitors (e.g., tolrestat, etc.), (5) antiinflammatory and/or antiallergy compounds (e.g., steroidal compounds such as betamethasone, clobetasone, dexamethasone, fluorometholone, hydrocortisone, prednisolone, etc. and nonsteroidal compounds such as antazoline, bromfenac, diclofenac, indomethacin, lodxamide, saprofen, sodium cromoglycate, etc., (6) artificial tear/dry eye therapies, comfort drops, irrigation fluids, etc. (e.g., physiological saline, water, or oils; all optionally containing polymeric compounds such as acetylcysteine, hydroxyethylcellulose, hydroxymellose, hyaluronic acid, polyvinyl alcohol, polyacrylic acid derivatives, etc.), (7) local anaesthetic compounds (e.g., amethocaine, lignocaine, oxbuprocaine, proxymetacaine, etc.), (8) compounds which assist in the healing of corneal surface defects (e.g., cyclosporine, diclofenac, urogastrone and growth factors such as epidermal growth factor), (9) mydriatics and cycloplegics (e.g., atropine, cyclopentolate, homatropine, hyoscine, tropicamide, etc.), (10) compounds for the treatment of pterygium (e.g., mitomycin C., collagenase inhibitors such as batimastat, etc.), (11) compounds for the treatment of macular degeneration and/or diabetic retinopathy and/or cataract prevention, (12) compounds for systemic effects following absorption into the bloodstream after ocular administration (e.g., insulin, narcotics, analgesics, anesthetics).

The terms "diagnostic" and "diagnostic agent" and the like are used interchangeably herein to describe any compound that is delivered to a patient in order to carry out a diagnostic test or assay on the patient. Such agents are often tagged with a radioactive or fluorescent component or other component which can be readily detected when administered to the patient. Exemplary diagnostic agents include, but are not limited to, methacholine, histamine, salt, specific allergens (such as pollen or pollen extracts), sulphites, and imaging agents for magnetic resonance imaging and/or scintigraphy. Diagnostic agents can be used to, for example, assess bronchial constriction in patients having or suspected of having cystic fibrosis or asthma. Radiolabelled aerosols can be used to diagnose pulmonary embolism, or to assess mucociliary clearance in various chronic obstructive diseases of the lung. Other diagnostic compounds include sensory compounds, including biocompatible compounds with distinctive taste, smell, or color, e.g., to assess the efficacy of aerosol delivery. Diagnostic agents can also be used to assess ophthalmic conditions. Exemplary ocular diagnostic agents include, but are not limited to, such compounds as fluorescein or rose bengal. Diagnostic agents are described and disclosed in U.S. Pat. No. 5,792,057.

The term "formulation" is intended to encompass any drug or diagnostic agent formulation which is delivered to a patient using the present invention. Such formulations generally include the drug or diagnostic agent present within a pharmaceutically acceptable inert carrier. The formulation is generally in a liquid flowable form which can be readily aerosolized, the particles having a particle size in the range of 0.5 to 12 microns in diameter for respiratory administration. Formulations can be administered to the patient using device of the invention can be administered by nasal, intrapulmonary, or ocular delivery.

The terms "aerosol," "aerosolized formulation," and the like, are used interchangeably herein to describe a volume of air which has suspended within it particles of a formulation comprising a drug or diagnostic agent. The particles preferably have a diameter in the range of 0.5 to 12 microns, for respiratory therapy, or in the range of 15 to 50 microns for ocular therapy.

The term "aerosol-free air" is used to describe a volume of air which is substantially free of other material and, in particular, substantially free of particles of aerosolized drug.

The term "dosing event" shall be interpreted to mean the administration of drug or diagnostic agent to a patient by the ocular or respiratory (e.g., nasal or intrapulmonary) route of administration (i.e., application of a formulation to the patient's eye or to the patient's respiratory tract by inhalation of aerosolized particles) which event may encompass one or more releases of drug or diagnostic agent formulation from a dispensing device over a period of time of 15 minutes or less, preferably 10 minutes or less, and more preferably 5 minutes or less, during which period multiple administrations (e.g., applications to the eye or inhalations) may be made by the patient and multiple doses of drug or diagnostic agent may be released and administered. A dosing event shall involve the administration of drug or diagnostic formulation to the patient in an amount of about 10 μl to about 1,000 μl in a single dosing event. Depending on the drug concentration in the formulation, a single package may not contain sufficient drug for therapy or diagnosis. Accordingly, a dosing event may include the release of drug or diagnostic agent contained from several containers of a package held in a cassette or the drug or diagnostic agent contained within a plurality of such containers when the containers are administered over a period of time, e.g., within 5 to 10 minutes of each other, preferably within 1-2 minutes of each other.

The term "velocity of the drug" or "velocity of particles" shall mean the average speed of particles of drug or diagnostic agent formulation moving from a release point such as the porous membrane of the nozzle or a valve to a patient's mouth or eye. In a preferred embodiment pertaining to respiratory therapy, the relative velocity of the particles is zero or substantially zero with reference to the flow created by patient inhalation.

The term "bulk flow rate" shall mean the average velocity at which air moves through a channel.

The term "flow boundary layer" shall mean a set of points defining a layer above the inner surface of a channel through which air flows wherein the air flow rate below the boundary layer is substantially below the bulk flow rate, e.g., 50% or less than the bulk flow rate.

The term "carrier" shall mean a flowable, pharmaceutically acceptable excipient material, which is not in itself pharmaceutically active. The carrier is preferably a liquid, flowable material, in which a drug or diagnostic agent is suspended in or more preferably dissolved in. Useful carriers do not adversely interact with the drug or diagnostic agent and have properties which allow for the formation of aerosolized particles, which particles preferably have a diameter in the range of 0.5 to 12.0 microns that are generated by forcing a formulation comprising the carrier and drug or diagnostic agent through pores having an unflexed diameter of 0.25 to 6.0 microns for delivery to the respiratory tract. Similarly, a useful carrier for delivery to the eye does not adversely interact with the drug or diagnostic agent and has properties which allow for the formation of aerosolized particles, which particles preferably have a diameter of 15 to 50 microns and are generated by forcing the formulation comprising the carrier and drug or diagnostic agent through pores 7.5 to 25 microns in relaxed diameter. Preferred carriers include water, ethanol, saline solutions and mixtures thereof, with pure water being preferred. Other carriers can be used provided that they can be formulated to create a suitable aerosol and do not adversely affect human tissue or the drug or diagnostic agent to be delivered.

The term "measuring" describes an event whereby the (1) total lung capacity, (2) inspiratory flow rate or (3) inspiratory volume of the patient is measured and/or calculated and the information used in order to determine an optimal point in the inspiratory cycle at which to release an aerosolized and/or aerosol-free volume of air. An actual measurement of both rate and volume may be made or the rate can be directly measured and the volume calculated based on the measured rate. The total lung capacity can be measured or calculated based on the patient's height, sex and age. It is also preferable to continue measuring inspiratory flow during and after any drug delivery and to record inspiratory flow rate and volume before, during and after the release of drug. Such reading makes it possible to determine if drug or diagnostic agent was properly delivered to the patient.

The term "monitoring" shall mean measuring lung functions such as inspiratory flow, inspiratory flow rate, and/or inspiratory volume so that a patient's lung function as defined herein, can be evaluated before and/or after drug delivery thereby making it possible to evaluate the effect of drug delivery on, for example, the patient's lung function.

The term "inspiratory flow profile" shall be interpreted to mean data calculated in one or more events measuring inspiratory flow and cumulative volume, which profile can be used to determine a point within a patient's inspiratory cycle which is optimal for the release of drug to be delivered to a patient. An optimal point within the inspiratory cycle for the release of an aerosol volume is based, in part, on (1) a point most likely to deliver the aerosol volume to a particular area of a patient's respiratory tract, in part on (2) a point within the inspiratory cycle likely to result in the maximum delivery of drug and, in part, on (3) a point in the cycle most likely to result in the delivery of a reproducible amount of drug to the patient at each release of drug. The criteria 1-3 are listed in a preferred order of importance. However, the order of importance can change based on circumstances. The area of the respiratory tract being treated is determined by adjusting the volume of aerosol-containing or aerosol-free air and/or by adjusting the particle size of the aerosol. The repeatability is determined by releasing at the same point in the respiratory cycle each time drug is released. To provide for greater efficiency in delivery, the drug delivery point is selected within given parameters.

The terms "formulation" and "flowable formulation" and the like are used interchangeably herein to describe any pharmaceutically active drug (e.g., a respiratory drug, or drug that acts locally or systemically, and that is suitable for respiratory delivery) or diagnostic agent combined with a pharmaceutically acceptable carrier in flowable form having properties such that it can be aerosolized to particles having a diameter of 0.5 to 12.0 microns for respiratory therapy, or 15 to 75 microns for ocular therapy. Flowable formulations include powders and liquids. Flowable formulations are preferably solutions, e.g., aqueous solutions, ethanolic solutions, aqueous/ethanolic solutions, saline solutions, colloidal suspensions and microcrystalline suspensions. Preferred formulations are drug(s) and/or diagnostic agent(s) dissolved in a liquid, preferably in water.

The term "substantially dry" shall mean that particles of formulation include an amount of carrier (e.g., water or ethanol) which is equal to (in weight) or less than the amount of drug or diagnostic agent in the particle, more preferably it means free water is not present.

The terms "aerosolized particles" and "aerosolized particles of formulation" shall mean particles of formulation comprised of carrier and drug and/or diagnostic agent that are formed upon forcing the formulation through a nozzle, which nozzle comprises a flexible porous membrane. Where respiratory therapy is desired, the particles are of a sufficiently small size such that when the particles are formed, they remain suspended in the air for a sufficient amount of time for inhalation by the patient through his nose or mouth. Where ocular therapy is desired, the particles formed are of a size optimal for application to the eye. Preferably, particles for respiratory delivery have a diameter of from about 0.5 micron to about 12 microns, and are generated by forcing the formulation through the pores of a flexible porous membrane, where the pores have an unflexed exit aperture diameter in the range of about 0.25 micron to about 6.0 microns. More preferably, the particles for respiratory delivery have a diameter of about 1.0 to 8.0 microns with the particles created by being moved through pores having an unflexed exit aperture diameter of about 0.5 to about 4 microns. For ocular delivery, the particles have a diameter from about 15 micron to about 75 microns, and are generated by forcing the formulation through the pores of a flexible porous membrane, where the pores have an unflexed exit aperture diameter in the range of about 5 micron to about 50 microns. More preferably, the particles for ocular delivery have a diameter of about 15 to 50 microns, and can be generated by forcing the formulation through flexible membrane pores having an unflexed exit aperture diameter of about 7.5 to about 25 microns. In either respiratory or ocular delivery, the flexible membrane pores are present at about 10 to 10,000 pores over an area in size of from about 1 sq. millimeter to about 1 sq. centimeter, preferably from about $1 \times 10^1$ to about $1 \times 10^4$ pores per square millimeter, more preferably from about $1 \times 10^2$ to about $3 \times 10^4$ pores per square millimeter, and the low resistance filter has an opening density in the range of 20 to 1,000,000 pores over an area of about one square millimeter.

The term "substantially through" with reference to the pores being formed in the membrane or material shall mean pores which either completely traverse the thickness of the membrane or are formed to have a thin peelable layer over their exit aperture. The pores formed with a peelable layer over their exit apertures are formed so as to peel outward at a substantially lower pressure than would be required to rupture the membrane in the nonporous areas.

An "individual", "subject", or "patient", used interchangeably herein, is a mammal, preferably a human.

Aerosolization Nozzles Comprising Specialized Pore Structures

The present invention provides thin sheets of membrane comprising specialized pore structures. These membranes are useful as aerosolization nozzles. The nozzles of the invention comprise membranes having a plurality of pores through which a flowable formulation is aerosolized for delivery to a subject. The plurality of pores passes through a "nozzle area" of the membrane, i.e., the area of the membrane through which the formulation is extruded and aerosolized. The material used may be any material from which suitable pores can be formed and which does not adversely interact with other components of the delivery device, particularly with the formulation being administered.

Pore Characteristics and Configurations

A critical feature of the membranes comprising specialized pore structures of the invention is the entrance aperture diameter to exit aperture diameter ratio of the pore, which in turn relates to the pressure needed to generate an aerosol. The ratio of the entrance aperture diameter to exit aperture diameter of these pores is significantly higher than that previously achieved. Accordingly, the present invention provides nozzles having pores with entrance aperture diameter to exit diameter ratio of at least about 10:1, more preferably at least about 12.5:1, more preferably at least about 15:1, more preferably at least about 20:1, more preferably at least about 25:1, up to about 100:1.

The pores can be of any shape, including, but not limited to, multi-step and tapered. Tapered pores are generally conical, where "conical" means that the pores are larger on one side of the membrane than on the other side, and that the diameter decreases in a continuous, linear fashion, i.e., a smooth curve, and includes instances where the cross-section of the pores is conical or curved. Multi-step pores can have two, three, four, or more steps, as necessary to achieve a reduction in the pressure needed to generate an aerosol. The number of steps is not critical to the aerosolization nozzles of the present invention. The height and aperture size of each pore step may depend upon the thickness of the membrane material. In some embodiments, the pore step adjacent to the entrance side of the membrane has a height of from about 20% to about 90%, usually from about 40% to about 80%, of the thickness of the material. Each pore step may be roughly cylindrical or conical in shape, where "cylindrical" means that the steps pass perpendicularly through the membrane and have approximately the same diameter throughout their length, and "conical" means that the pores are larger on one side of the membrane than on the other side, and that the diameter decreases in a continuous, linear fashion, and includes instances where the cross-section of the pores is conical or curved. In some embodiments, the through-steps are conical.

When the pores, pore steps, or through-steps of the pores are conical, the wider diameter of the cone is found on the entrance side of the pore to which the formulation is applied under pressure, while the smaller diameter of the cone is closer to the exit side of the pore from which aerosolization occurs. The exit aperture size of the pores is preferably uniform; following the methods taught herein, the variability in exit aperture size is generally less than about 10%, usually less than about 5%. The nozzle may be provided as an integral part of the formulation packaging, or may be provided separately, for example integrally with the inhalation device, or wound on a roll for disposable use.

The pore structures described herein are formed in a membrane for use in an aerosolization device, and allow generation of aerosols at significantly lower aerosolization pressures than was previously achievable. Accordingly, the pore structures of the present invention, when formed in membranes used in an aerosolization device, allow aerosolization of a flowable formulation at extrusion pressures less than about 500 psi, generally in a range of about 100 psi to about 500 psi, usually in a range of about 200 psi to about 400 psi. In general, the amount of pressure required is greater than about 100 psi, and less than about 500 psi.

For respiratory delivery, the pores are formed so as to have an unflexed exit aperture diameter from about 0.25 to 6.0 microns in size, preferably 0.5 to 5.0 microns. When the pores have this size, the droplets that are formed will have a diameter about twice the diameter of the pore size. In some cases, it may be desirable to generate aerosols having an aerodynamic size in a particular range. Thus, it may be of interest to generate particles having an aerodynamic size in the range of 1-3 µm, 4-6 µm, or 7-10 µm. Exit pore aperture sizes would be adjusted accordingly.

The terms "particle diameter", "particle size" and the like are used interchangeably herein to refer to particle size as given in the "aerodynamic" size of the particle. The aerodynamic diameter is a measurement of a particle of unit density that has the same terminal sedimentation velocity in air under normal atmospheric conditions as the particle in question. When small (e.g., 1-50 micrometer diameter) particles are said to have the same diameter, they have the same terminal sedimentation velocity. This is pointed out in that it is difficult to accurately measure the diameter of small particles using current technology and the shape of such small particles may be continually changing. For ocular delivery, the pores are formed so as to have an unflexed exit aperture diameter in the range of 5 microns to 50 microns, preferably 7.5 to 25 microns.

The pores can be spaced from about 10 to about 1000 µm apart or more, but are preferably spaced from about 30 to about 70 µm apart, most preferably about 50 µm apart. The pore spacing is determined in part by the need to prevent the aerosol from adjacent pores from adversely interfering with each other, and in part to minimize the amount of membrane used and the associated manufacturing difficulties and costs. The pore spacing is preferably fairly uniform, with a variability in the interpore distance of preferably less than about 20%, more preferably less than about 10%, and most preferably about 2% or less (<1 µm variability for pores spaced 50 µm apart).

The pores in a nozzle area may be arranged in regular arrays, such as in rows or grids of pores at regular, substantially uniform distances from one another. In one embodiment of the invention, the pores are formed in a 7×48 array of pores spaced 50 µm apart.

A given membrane may have a plurality of nozzle areas, at a given distance from an adjacent nozzle area, and separated from adjacent nozzle area by a section of non-porous membrane. In some embodiments, the membrane is a strip comprising a plurality of nozzle areas separated from one another by non-porous membrane areas.

The amount of liquid being aerosolized is generally from about 10 µl to about 100 milliliters. In some embodiments, the amount of liquid is in a range of from about 5 milliliters (ml) to about 100 milliliters, from about 10 milliliters to about 90 milliliters, from about 20 milliliters to about 80 milliliters, from about 40 milliliters to about 60 milliliters. In other embodiments, the amount of liquid is in a range of from about 0.5 ml to about 10 ml, from about 1 ml to about 8 ml, from about 2 ml to about 6 ml. In still other embodiments, the amount of liquid is in a range of from about 10 µl to about 1000 µl from about 20 µl to about 100 µl.

The density of pores in the nozzle area ranges from 1 to about 1,000 pores, generally about 100 to about 900 pores, per square millimeter. In some embodiments, the pore density in the nozzle area is about 100 pores per square millimeter. In other embodiments, this density is about 200 pores per square millimeter.

The period of time over which the formulation is to be administered must also be considered. The delivery time is a critical parameter, as it is necessary to generate the aerosol during a sufficiently short period of time so that the aerosol may be targeted to a specific area of the respiratory tract during inspiration. For a given pore exit diameter and formulation pressure, hole number can be adjusted to control delivery time. Generally, aerosolization will occur within about 0.5 to about 5 seconds, usually in a range of about 1 second to about 2 seconds.

In one embodiment, the pores are incompletely formed so that a thin peelable layer remains covering the exit apertures of the pores. This peelable layer bursts outward upon forcible application of the drug formulation to the nozzle during drug delivery, permitting aerosolization of the formulation. The peelable layer of the pores is formed so as to have a breaking pressure significantly below that of the overall membrane, and the pressure at which the layer bursts is significantly below that applied in the normal course of drug administration, so that the pores burst substantially uniformly and completely. The incompletely formed pores may be formed by application of a thin layer of material to the outer side of the membrane after formation of complete pores, or by incompletely ablating holes through the membrane.

In another embodiment, the pores are provided with elevated areas surrounding the exit aperture, so as to prevent liquid from intruding from the outer surface of the membrane back into the pore and thereby disrupting aerosolization. The elevated areas may be of any shape, such as circular or rectangular, or may be irregularly shaped. The elevated areas can be constructed by any suitable means, for example by etching away portions of the outer layer of the membrane, by laser drilling procedures which lead to sputtering of material around the pores, by molding or casting, by deposition of material via a mask in locations where pores are to be formed, and the like.

A pore may be formed so as to have an elevated area via excimer laser ablation from the opposite side of the membrane. The formation of the elevated area via excimer laser ablation can be controlled by altering the pulse number: a minimal number of pulses used to penetrate the membrane will foam an elevated area around the aperture on the opposite side of the membrane; increasing the number of pulses will then remove this elevated area. For example, for a 25 micron thick polyimide membrane, 120 pulses of a 308 nm excimer laser at an energy density of 630 mJ/cm$^2$ will form a pore having an elevated area, while increasing the number of pulses above 150 will remove the elevated area and slightly widen the pore aperture. The elevated areas may be of any suitable dimensions, but preferably extend significantly less than the interpore distance so as to provide lower areas where fluid is sequestered. The elevated areas can be made from any suitable material, for example the material comprising the bulk of the membrane, or may be made from materials with desirable properties such as hydrophobicity or solvent or drug repellence so as to repel the drug formulation from entering the exit aperture of the pores.

Membrane Materials and Characteristics

The membrane material is preferably hydrophobic and includes, but is not limited to, materials such as polycarbonates, polyimides, polyamides, polysulfone, polyolefin, polyurethane, polyethers, polyether imides, polyethylene and polyesters which may have the pores formed therein by any suitable method including, but not limited to, laser drilling, electron discharge machining, or anisotropic etching through a thin film of metal or other suitable material. Co-polymers of the foregoing can also be used. Shape memory polymers, which are known in the art and have been described in, inter alia, U.S. Pat. No. 5,910,357, can also be used. Preferably, the membrane is one that does not interact chemically with the substance being aerosolized, or the aerosolization solvent. The membrane preferably has sufficient structural integrity so that it is maintained intact (will not rupture) when subjected to force in the amount up to about 580 psi, preferably of up to about 725 psi, while the formulation is forced through the pores.

In some embodiments, the material is a flexible polymeric organic material, for example a polyether, polycarbonate, polyimide, polyether imide, polyethylene or polyester. Flexibility of the material is preferred so that the nozzle can adopt a convex shape and protrude into the airstream upon application of pressure, thus forming the aerosol away from the static boundary layer of air. Material which is substantially non-flexible can also be used, and, if such material is used, is preferably shaped to have a convex configuration.

As would be apparent to those skilled in the art who read this disclosure, the nozzle area is the porous membrane area. That area may be integral with surrounding sheet material (i.e. a porous area of sheet or tape) or be a separate membrane covering an opening in a thin sheet or tape (i.e., a porous membrane sheet separate from the surrounding sheet or tape). In some embodiments, the porous membrane is covered by a removable cover sheet detachably connected to the porous membrane.

The thickness of the membrane affects both the manufacturing of the nozzles and containers as well as the pressure required to generate the desired aerosol during administration. Thinner membranes require less pressure to generate an aerosol, but are conversely more difficult to handle during manufacturing, for example in laminating the membrane to other components of the formulation container. The membrane is preferably about 10 to about 100 µm in thickness, from about 15 to about 40 micrometers, from about 20 to about 30 micrometers, more preferably from about 12 to about 45 µm in thickness. In one embodiment, the membrane material is a 25 µm thick film of polyimide. Considerations for the membrane material include the ease of manufacture in combination with the formulation container, flexibility of the membrane, and the pressure required to generate an aerosol from pores spanning a membrane of a given material, thickness and flexibility.

Methods for Generating Pores in Reduced Pressure Extrusion Nozzles

The present invention provides methods for generating specialized pore structures as described above in thin sheets of material. Suitable methods include, but are not limited to, laser ablation (micromachining), anisotropic etching, and electron discharge machining. Pores can be formed by a single-step or a multi-step method. These methods include, but are not limited to, a multi-step process; a one-step process using a single, variable-density mask; and dithering. These methods are described below. Membranes comprising these specialized pore structures are useful in aerosolization nozzles. Accordingly, the invention provides methods of making aerosolization nozzles. These nozzles can be used in reduced-pressure aerosolization devices.

In some embodiments, laser ablation is used to form tapered or multi-step pores as described herein in the membrane. The particular laser source used in the method of the invention will to some extent be determined by the material in which the pores are to be formed. Generally, the laser source must supply a sufficient amount of energy of a wavelength which can form an effective aerosolization nozzle in the material being ablated. Typically, for an organic polymer membrane, the wavelength is from about 150 nm to about 360 nm.

The output of the particular laser source can be manipulated in a variety of ways prior to being applied to the material. For example, the frequency can doubled or tripled using, for example, a lithium triborate crystal or series of crystals, or a combination thereof. This laser beam can be further split into multiple beams to create multiple pores simultaneously. The beam can also be directed through a mask or spatially filtered, and can also be expanded prior to focusing.

One laser effective for such nozzles is a neodymium-yttrium aluminum garnet laser. This laser can be configured to provide a pulsed ultraviolet wavelength light source which provides sufficiently high peak power in short pulses to permit precise ablation in a thin material. The beam profile from this laser is radially symmetric which tends to produce radially symmetric pores.

Another laser effective for creating pores in materials such as polyethers and polyimides is an excimer laser. This laser also produces ultraviolet wavelength light. However, the beam is not radially symmetrical but is projected through a mask to simultaneously drill one or more conical or cylindrical holes. In some embodiments, the laser source is an excimer laser providing a wavelength of 308 nm. The energy density used for such a laser typically ranges from about 300 to about 800 mJ/cm$^2$, from about 400 mJ/cm$^2$ to about 700 mJ/cm$^2$, from about 500 mJ/cm$^2$ to about 700 mJ/cm$^2$. In some embodiments, the energy density is about 630 mJ/cm$^2$. Using such a laser on a 25 µm thick polyimide membrane, the number of pulses is typically about 40 to about 200. Those skilled in the art will readily appreciate that these parameters can be varied, depending on the thickness of the membrane being drilled.

The methods of the present invention for producing a porous membrane, generally comprise the steps of: directing laser energy onto an entrance surface of a membrane and continuing to direct the energy until the laser has created a pore having an entrance aperture and an exit aperture having a pore entrance aperture size and a pore exit aperture size, wherein the ratio of pore entrance aperture size to pore exit aperture size is at least about 10:1. The directing of laser energy can be repeated a plurality of times, by repositioning the laser energy for each directing step, or by repositioning the membrane for each directing step.

Multi-Step Methods

A pore as described herein can be made by multi-step methods. The pores are ablated in stepwise fashion from the entrance side of the membrane to form steps of decreasing diameter toward the exit side of the membrane. This decreases the total number of laser pulses necessary to generate a pore having a wider entrance aperture and a narrower exit aperture, and allows for entrance aperture diameters which could not be achieved via single-step methods for a given exit aperture diameter.

The multistep methods generally comprise the steps of: directing laser energy onto a first surface of a membrane having a thickness X and continuing to direct the energy until the laser has created an entrance hole into the first surface having a depth of X/Y wherein Y is greater than X and less than 10X and the entrance hole has a diameter D; directing laser energy onto a second surface at the bottom of the hole until the laser has created an exit hole having a diameter D/d wherein d is greater than D and is less than 10D wherein the depth of the entrance hole combined with the depth of the exit hole is a depth in a range of from X to 0.95X. In general, Y is in a range of about 4X to about 0.5X, usually in a range of about 2X to about 1.0X. Typically Y is about 2X±10%.

To form a multi-step pore, a first pore step is formed to a depth h1 (resulting in a first pore step height h1) in a membrane, starting from the entrance side of the membrane, wherein h1 is less than the thickness of the membrane, and is generally about 20% to about 90%, generally about 40% to about 80% of the thickness of the membrane. The first pore step has an entrance aperture size and an exit aperture size. A second pore step is then formed to a depth h2 (resulting in a second pore step height h2), which in turn has an entrance aperture size and an exit aperture size. The second pore step entrance aperture size is generally about 20% to about 90%, generally about 40% to about 80% of the first pore step aperture size. The second pore step exit aperture can also be the pore exit, or can lead to a third pore step. In general, the entrance aperture size of a given pore step is about 20% to about 90%, generally about 40% to about 80%, of the exit aperture size of the preceding, membrane entrance side-proximal, pore step. This process is shown schematically in FIG. 2.

For example, a two-step pore can be formed by directing about 40-60 pulses of an excimer laser beam at a fluence level of 625 mJ/cm$^2$ so as to form a 25 µm entrance aperture diameter first pore step to a depth of 10-20 µm through a 25 µm thick polyimide film, resulting in a first pore step having a height of 10-20 µm. A second beam of similar fluence can then be directed coaxially, or nearly coaxially, for about 50-75 pulses into the partially ablated first pore step so as to have a 4-6 µm entrance aperture diameter from the bottom of the partially ablated first pore step through to the exit side of the membrane to produce a pore having an exit aperture of about 1.0 to about 1.5 µm, e.g. 1.2 µm, thereby forming a second pore step having a 4-6 µm entrance aperture diameter and a 1.0 to about 1.5 µm exit diameter. The resulting multi-step pore has an entrance aperture diameter to exit aperture diameter ratio of about 20:1 to about 25:1.

Each step which does not pass through to the exit side of the membrane can have one or more further steps or through-steps ablated from its exit side terminus. Up to the entire nozzle area of the membrane can be ablated in forming the first step or series of steps. The entire array of through-steps can then be ablated in this ablated area. The result is that, for a two-step process, the entire nozzle area of a 25 µm thick polyimide film can be ablated in the first step to a depth of 10-20 µm, and the entire array of through-steps can then be ablated through the remainder of the membrane.

Single-Step Methods

Any of a number of single-step methods are available for use in generating pore structures for reduced-pressure aerosolization.

One such method makes use of a single mask having a variable-density dot pattern, as described in U.S. Pat. No. 5,417,897, which method is specific to making a hole for an ink jet printer nozzle. Using this method, a mask may comprise an open central region, which allows 100% transmission of the laser energy. Surrounding and continuous with the open central region is a second region in which the mask material is arranged in a pattern of opaque dots which act to partially shield a membrane in which pores are to be formed. By selecting a density of opaque dots in the peripheral region around the central opening, the central portion of each nozzle formed will be completely ablated through, and the peripheral portions of the nozzle will be only partially ablated. Transmission of laser energy in the first peripheral region is about 20 to about 65%. A second peripheral region can be made such that the transmission is less than in the first peripheral region. By varying the density of the opaque dots in the first and (optional) second peripheral regions, the pore formed in the nozzle membrane can be made to a desired shape. This process is sometimes referred to herein as a "Grayscale process".

Another method for making pores having the characteristics described above involves use of dithering, or rotating an optical mirror to rotate a laser beam during the ablation process. By changing the rotation of the mirror, the laser beam can be focused onto an area of successively decreasing size through the thickness of the membrane, thereby forming a reduced-pressure aerosolization pore having the characteristics described herein. The dithering method has been amply described in the literature, including, for example, in U.S. Pat. No. 4,894,115.

Nozzle and Container Configurations

The present invention provides containers for aerosolizing a flowable formulation, the containers comprising the nozzles comprising specialized pore structures, as described above. Further provided are methods of making the containers.

In general, the nozzle comprised of a porous membrane according to the invention can be used in conjunction with any container suitable for containing a drug or diagnostic agent formulation of interest. The container can be, for example, a single-dose container or a multidose container. Examples of single-dose and multi-dose containers are provided in Example 2 and in FIGS. 6 and 7. The containers can be refillable, reusable, and/or disposable. Preferably, the container is disposable. The container can be designed for storage and delivery of a drug or diagnostic agent that is dry, substantially dry, liquid, or in the form of a suspension. The container may be any desired size. In most cases the size of the container is not directly related to the amount of drug or diagnostic agent being delivered in that most formulations include relatively large amounts of excipient material, e.g., water or a saline solution. Accordingly, a given size container could include a wide range of different doses by varying drug (or diagnostic agent) concentration.

The present invention provides a container for aerosolizing a flowable liquid formulation for delivery to a patient, comprising: (a) a sheet of flexible membrane material having an entrance side to which the formulation is applied under a pressure, an exit side from which aerosol is released, and a nozzle area, which nozzle area has a plurality of pores therein through which the formulation is extruded, each of the pores having an exit aperture and an entrance aperture having a pore entrance aperture size and a pore exit aperture size, wherein the ratio of pore entrance aperture size to pore exit aperture size is at least about 10:1; (b) container walls connected to the sheet wherein a wall of the container is collapsible by the application of a force; and (c) a liquid formulation held within the container walls.

The present invention further provides methods for making the aerosolization containers as described herein, generally comprising positioning a sheet of flexible membrane material, which comprises nozzle areas having pore structures as provided in the present invention, adjacent to a container comprising a formulation, such that the nozzle is connected to the container, wherein the container comprises at least one wall collapsible by the application of a force.

Because the container comprises a nozzle as described above, a force of about 500 pounds per square inch (psi) or less collapses the container and forces the formulation out of pores of the membrane and aerosolizes the formulation. Generally, the amount of pressure required to collapse the container, force the formulation out of the pores of the membrane, and aerosolize the formulation is in a range of about 100 psi to about 500 psi, usually in a range of about 200 psi to about 400 psi. In general, the amount of pressure required is greater than about 100 psi, and less than about 500 psi.

Generally, the amount of liquid formulation in the container is generally from about 10 µl to about 100 milliliters. In some embodiments, the amount of liquid is in a range of from about 5 milliliters (ml) to about 100 milliliters, from about 10 milliliters to about 90 milliliters, from about 20 milliliters to about 80 milliliters, from about 40 milliliters to about 60 milliliters. In other embodiments, the amount of liquid is in a range of from about 0.5 ml to about 10 ml, from about 1 ml to about 8 ml, from about 2 ml to about 6 ml. In still other embodiments, the amount of liquid is in a range of from about 10 µl to about 1000 µl, from about 20 µl to about 100 µl.

The time required to aerosolize the formulation is generally in the range of 0.5 second to 5 seconds, generally about 1 second to about 2 seconds.

The present invention further provides a disposable container comprising: (a) at least one wall which is collapsible by the application of a force and having at least one opening, wherein the opening leads to an open channel having an end; (b) a nozzle as described herein positioned at the end of the open channel, the nozzle comprising: a sheet of flexible membrane material having an entrance side to which said formulation is applied under a pressure, an exit side from which aerosol is released, and a nozzle area, which nozzle area has a plurality of pores therein through which the formulation is extruded, each of the pores having an exit aperture and an entrance aperture having a pore entrance aperture size and a pore exit aperture size, wherein the ratio of pore entrance aperture size to pore exit aperture size is at least about 10:1; and (c) formulation in an amount of 100 milliliters or less in the container. In some embodiments, the open channel comprises a seal which is peeled open upon application of a force exerted upon the collapsible wall. In other embodiments, the disposable container further comprises a low resistance filter positioned between the seal and the nozzle. The invention further provides a disposable package comprising one or a plurality of a container of the invention.

The container can also be one that provides for storage of a drug or diagnostic agent in a dry or substantially dry form until the time of administration, at which point, if desired, the drug or diagnostic agent can be mixed with water or other liquid. An exemplary dual compartment container for carrying out such mixing of dry drug with liquid just prior to administration is described in U.S. Pat. No. 5,709,202, incorporated herein by reference with respect to such containers.

In a preferred embodiment, the containers useful with the invention comprise a single-use, single-dose, disposable container that holds a formulation for delivery to a patient and has a collapsible wall. In addition, the container can be configured in the same package with a porous membrane and a low resistance filter, where the low resistance filter is positioned between the porous membrane and a formulation contained in the container. The container is preferably disposable after a single use in the delivery of the formulation contained therein.

In one embodiment, the container is shaped by a collapsible wall. The container has an opening covered by a nozzle comprised of a flexible porous membrane. The exit apertures of the pores of the nozzle are surrounded by elevated areas which prevent intrusion of fluid back into the pores. The container includes an opening which leads to an open channel which channel includes an abutment (or peelable seal) which is peeled open upon the application of force created by formulation being forced from the container. A low resistance filter can be positioned between the formulation and the peelable seal. The filter has a porosity such that the presence of the filter does not substantially increase the pressure required to generate an aerosol by forcing the formulation through the porous membrane of the nozzle. When the abutment is peeled open, the formulation flows to an area adjacent to the nozzle's flexible porous membrane and is prevented from flowing further in the channel by a nonbreakable abutment.

Figure 6:
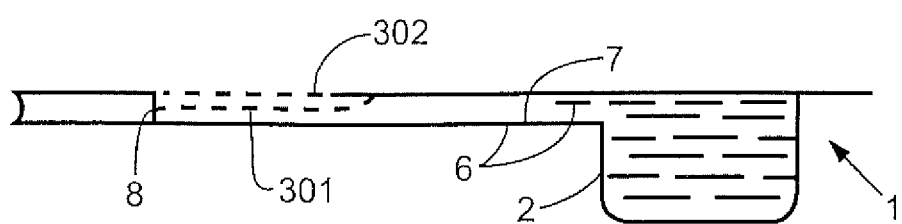
FIG. 6 is a cross-sectional view of a container of a preferred embodiment of a container of the invention.
Figure 7:
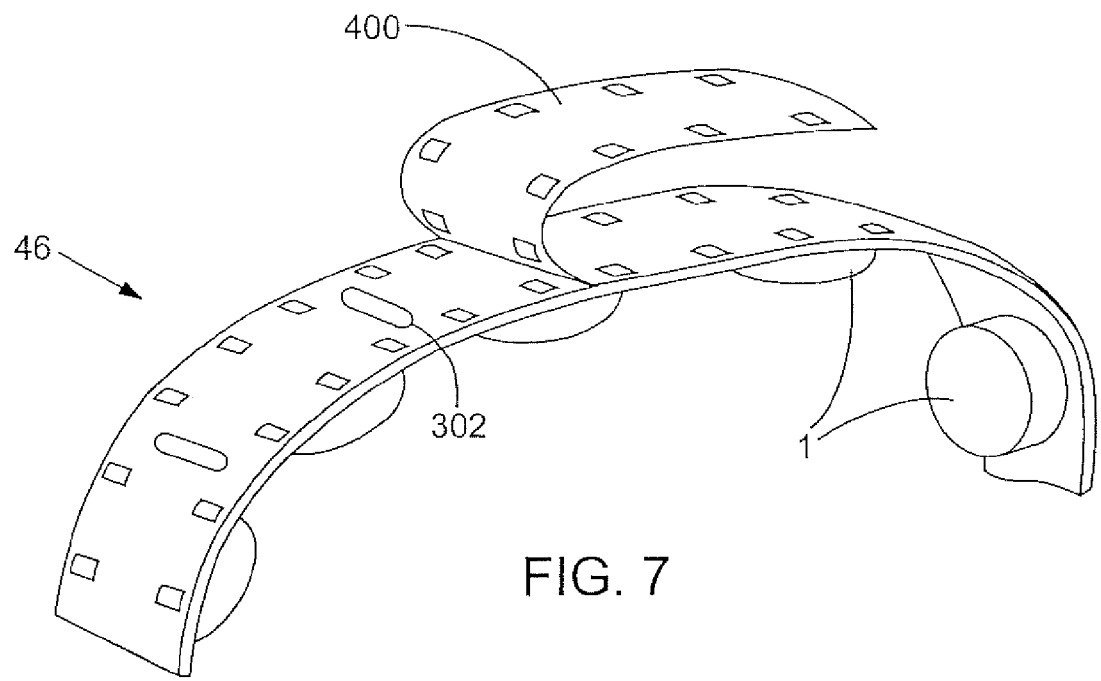
FIG. 7 is a top plan view of a disposable package of the invention.

FIG. 6 is a cross-sectional view of a preferred embodiment of a disposable container 1 of the invention. The container is shaped by a collapsible wall 2. The container 1 includes an opening which leads to an open channel 6, which channel 6 includes an abutment (or peelable seal) 7 which is peeled open upon the application of force created by formulation 5 being forced from the container. A low resistance filter 301 is positioned between the peelable seal 7 and the nozzle 302. When the peelable seal 7 is broken, the formulation 5 flows to an area adjacent the low resistance filter 301, through the low resistance filter 301, if present, and out the nozzle 302 to form an aerosol. The formulation 5 is prevented from flowing further in the channel 6 by a nonbreakable abutment 8. A number of containers can be connected together to form a package 46 as shown in FIG. 7. The package 46 is shown in the form of an elongated tape, but can be in any configuration (e.g., circular, square, rectangular, etc.). Furthermore, the package 46 is shown comprising a single row of containers, but can comprise two or more rows.

Figure 8:
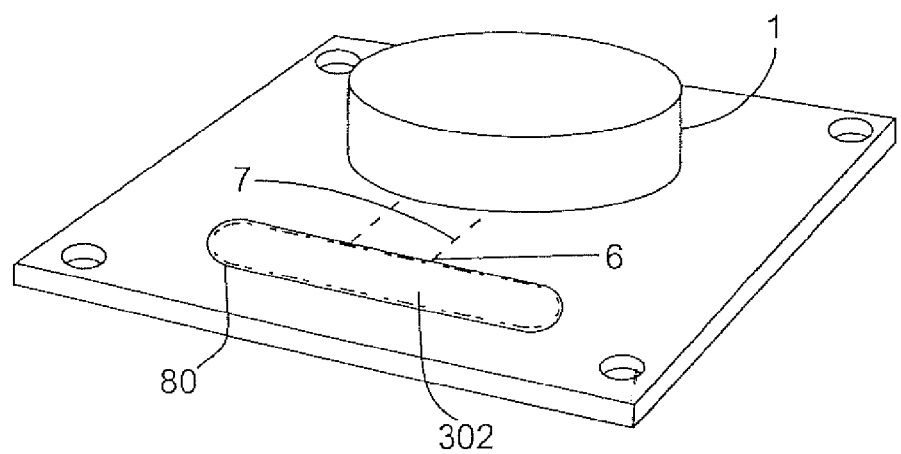
FIG. 8 is a cross-sectional view of a portion of a disposable package of the invention.
Figure 9:
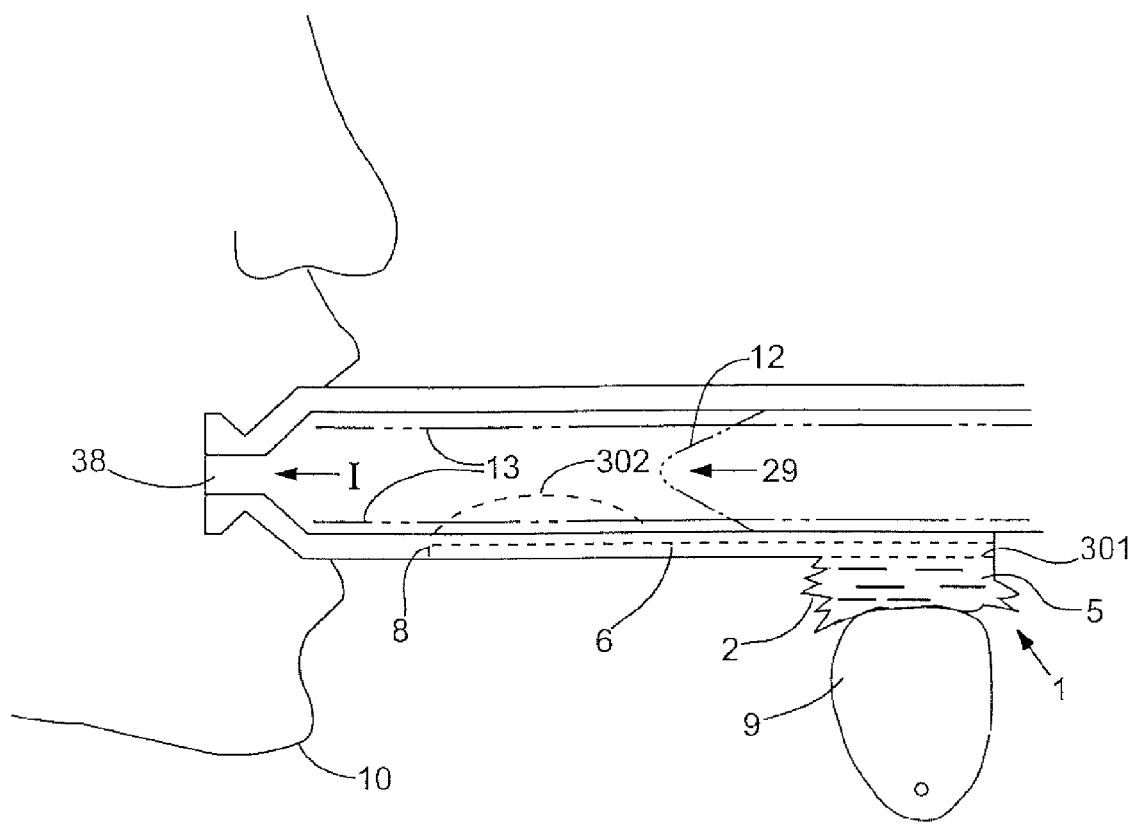
FIG. 9 is a cross-sectional view of a container used in a channel of an aerosol delivery device.

FIG. 9 is a cross-sectional view of the disposable container 1 of FIG. 6 in use for respiratory therapy. The wall 2 is being compressed by a mechanical component such as the cam 9, as shown in FIG. 9. The cam may be driven by a motor connected to gears which turn the cam 9 to bring the cam into contact with and apply the necessary force to the collapsible wall 2 of the container 1. The formulation 5 is forced through the low resistance filter 301, if present, into the open channel 6 (breaking the seal 7 shown in FIG. 8), and against and through the nozzle 302 causing the porous membrane of the nozzle 302 to protrude outward into a convex configuration as shown in FIG. 7. The cam 9 has been forced against the container wall 2 after a patient 10 begins inhalation in the direction of the arrow "I."

An exemplary method for using the aerosol delivery device 40, as shown in FIG. 9, is as follows. The patient 10 inhales through the mouth from a tubular channel 11. The velocity of the air moving through the flow path 29 of the channel 11 can be measured across the diameter of the channel to determine a flow profile 12, i.e., the air flowing through the channel 11 has a higher velocity further away from the inner surface of the channel. The air velocity immediately adjacent to the inner surface of the channel 11 (i.e., infinitely close to the surface) is very slow (i.e., approaches zero). A flow boundary layer 13 defines a set of points below which (in a direction from the channel center toward the inner surface of the channel) the flow of air is substantially below the bulk flow rate, i.e., 50% or less than the bulk flow rate.

As shown in FIG. 9, the convex shape that the flexible porous membrane of the nozzle 302 takes on during use plays an important role. Preferably, the upper surface of the flexible porous membrane of the nozzle 302 is substantially flush with (i.e., in substantially the same plane as) the inner surface of the channel 11 to allow air to flow freely. Thus, if the membrane of the nozzle 302 remained in place when the formulation 5 moved through the pores, the formulation would be released into the slow moving or substantially "dead air" below the boundary layer 13. However, when the formulation 5 is forced from the container 1 by force applied from a source such as a motor-driven cam 22, the formulation 5 presses against the flexible porous membrane of the nozzle 302 causing the porous membrane to convex outward beyond the plane of the resting surface of the nozzle's membrane 302 and beyond the plane of the inner surface of the channel 11. The convex upward distortion of the membrane of the nozzle 302 is important because it positions the pores of the membrane beyond the boundary layer 13 (shown in FIG. 9) into faster moving air of the channel 11.

A device similar to the device 40 of FIG. 9 can be similarly used to deliver a drug to the respiratory tract by nasal delivery. For example, the mouthpiece 30 and opening 38 are suitably modified to provide for delivery by nasal inhalation. Thus, the patient places the opening of the modified device into his nostril and, after inhalation, a dose of the drug is delivered to the respiratory tract of the patient in a manner similar to that described above.

Aerosol delivery of a drug to the eye can be accomplished using a device similar to the device 40 described above, with modifications. For example, the device 40 shown in FIG. 9 is modified such that the mouthpiece 30, opening 38, and channel are suitable for aerosol delivery to the surface of the patient's eye. The patient positions the device so that aerosol formulation exiting the opening 38 will contact the eye's surface; the channel is open at the opening end (opening 38) and is preferably closed at the end opposite the opening end. The device may additionally comprise a means to maintain the device in a stable position over the patient's eye and/or a means for detecting when the patient's eye is open. Upon activation of the device, a cam 9 (or other mechanical component) crushes the collapsible wall 2 of the container 1. The formulation 5 is forced through the filter 301, into the open channel 6 (breaking the seal 7), and against and through the nozzle 302, thereby generating an aerosol which is forced out of the device through an opening so as to come into contact with the surface of the eye.

The device of the invention can use a low resistance filter and a porous membrane to prevent clogging of the nozzle's porous membrane and to prevent the passage of undissolved particles or drug and/or other undesirable particles from being delivered to the patient. In general, the formulation is released from a container, passed through at least one low resistance filter, and then passed through a porous membrane of a nozzle. An aerosol is formed from the drug formulation when it exits the pores of the porous membrane, and the aerosol is delivered to the patient.

The nozzle can be included as components of a disposable package that is composed of a container that serves as a storage receptacle for the drug formulation, a porous membrane, and, optionally, a low resistance filter positioned between the drug formulation and the nozzle. Such filters are described and disclosed in U.S. Pat. No. 5,829,435 issued Nov. 3, 1998.

The nozzle can also be provided separate from the drug container and/or the disposable package. For example, the nozzle can be provided as a single disposable unit that can be inserted in the proper position relative to the container. The disposable nozzle can be inserted prior to use and can be disposed after each use or after a recommended number of uses. Alternatively, the nozzle can be provided as a separate ribbon or ribbons.

The formulation may be a low viscosity liquid formulation. The viscosity of the drug or diagnostic agent by itself or in combination with a carrier is not of particular importance except to note that the formulation must have characteristics such that the formulation can be forced out of openings to form an aerosol, e.g., when the formulation is forced through the flexible porous membrane it will form an aerosol preferably having a particle size in the range of about 0.1 to 12 microns for intrapulmonary delivery or in the range of 15 to 75 microns for ocular delivery.

Aerosol Delivery Devices

The present invention further provides aerosol delivery devices which comprise a container as described herein. In general, aerosol delivery devices useful with the invention comprise (a) a device for holding a formulation-containing container, preferably a disposable container, with at least one but preferably a number of containers, and (b) a mechanical mechanism for forcing the contents of a container (on the package) through a nozzle comprised of a porous membrane and having pore structures as provided by the present invention, optionally preceded by a low resistance filter. Where the device is used for respiratory delivery, the device can further comprise (c) a means for controlling the inspiratory flow profile, (d) a means for controlling the volume in which the drug or diagnostic agent is inhaled, (e) a switch for automatically releasing or firing the mechanical means to release a determined volume of aerosol and aerosol-free air when the inspiratory flow rate and/or volume reaches a predetermined point, (f) a means for holding and moving one package after another into a drug release position so that a new package is positioned in place for each release of drug, and (g) a source of power, e.g., spring, or conventional batteries or other source of electric power.

The present invention further provides methods for making aerosol delivery devices as described herein, generally comprising disposing a container as described herein in a holding device, wherein the holding device is coupled to a mechanical mechanism for forcing the contents of the container through the nozzle of the container.

Figure 10:
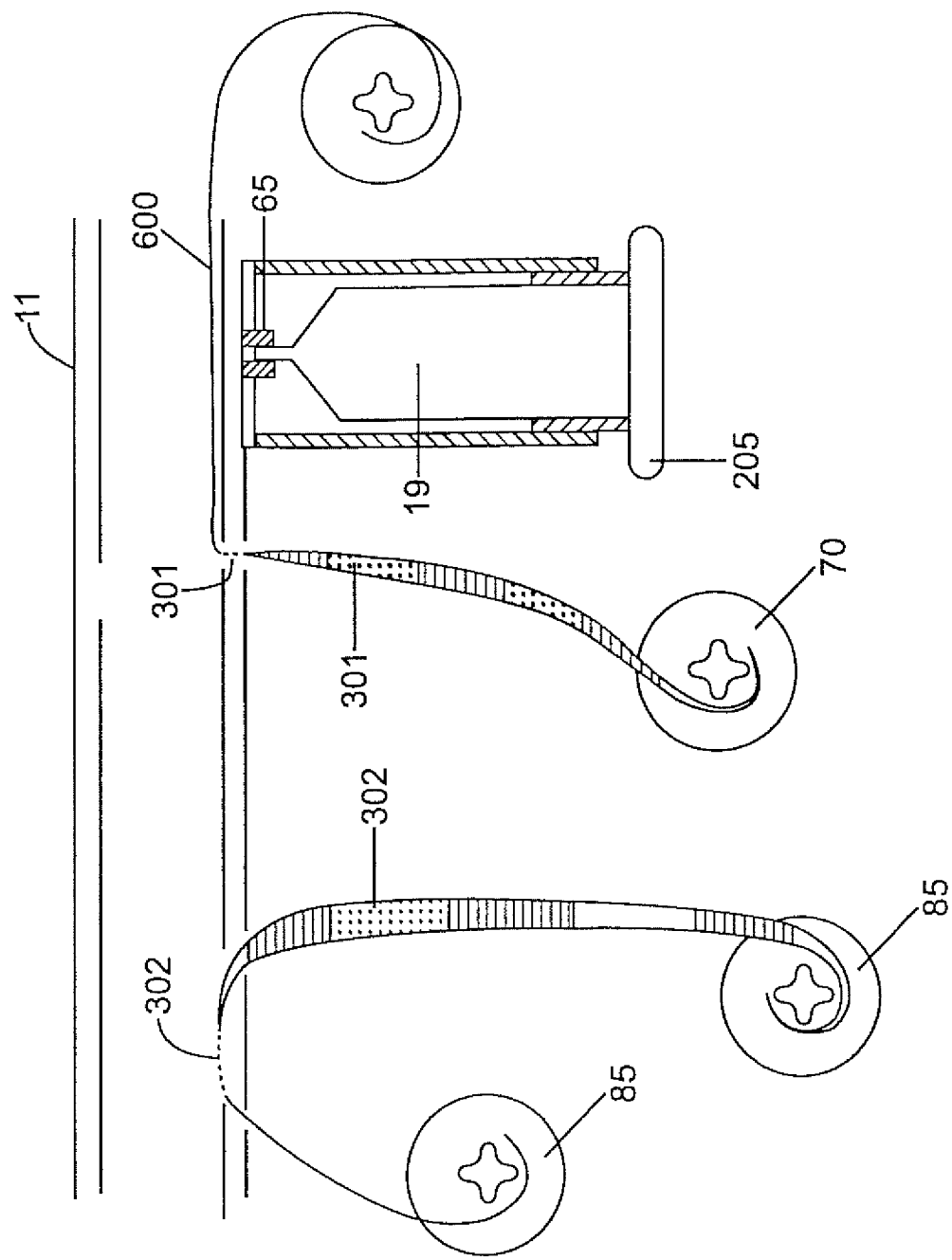
FIG. 10 is a cross-sectional view of an aerosol delivery device of the invention having a multidose container and a ribbon of low resistance filters and a ribbon of porous membranes.

FIG. 10 is a cross-sectional view of an aerosol delivery device of the invention having a multidose container and a ribbon of low resistance filters and a ribbon of porous membranes.

Figure 11:
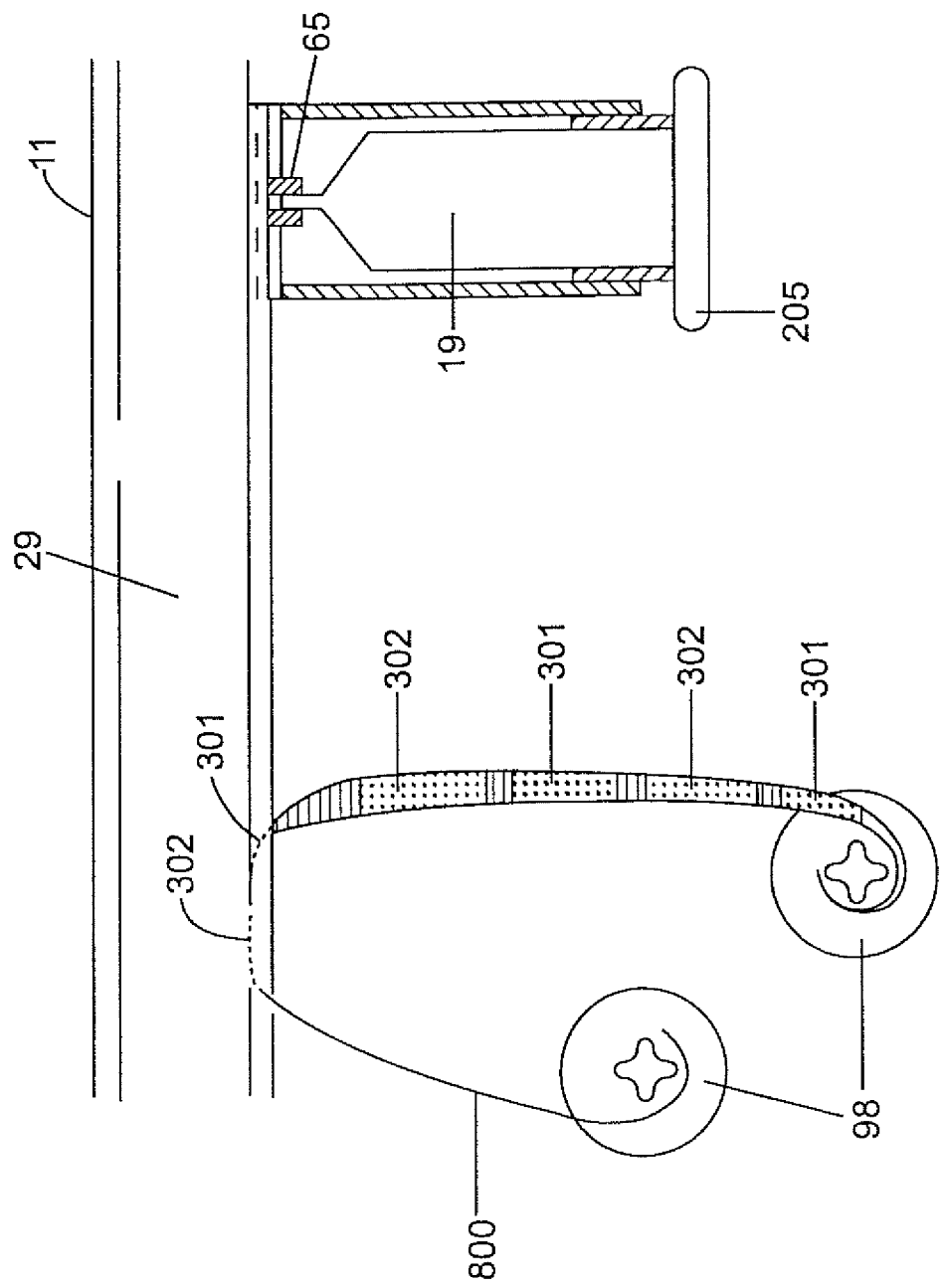
FIG. 11 is a cross-sectional view of an aerosol delivery device of the invention having a multidose container and single ribbon having both interconnected low resistance filters and nozzles comprised of porous membranes.

FIG. 11 is a cross-sectional view of an aerosol delivery device of the invention having a multidose container and single ribbon having both interconnected low resistance filters and nozzles comprised of porous membranes.

Figure 12:
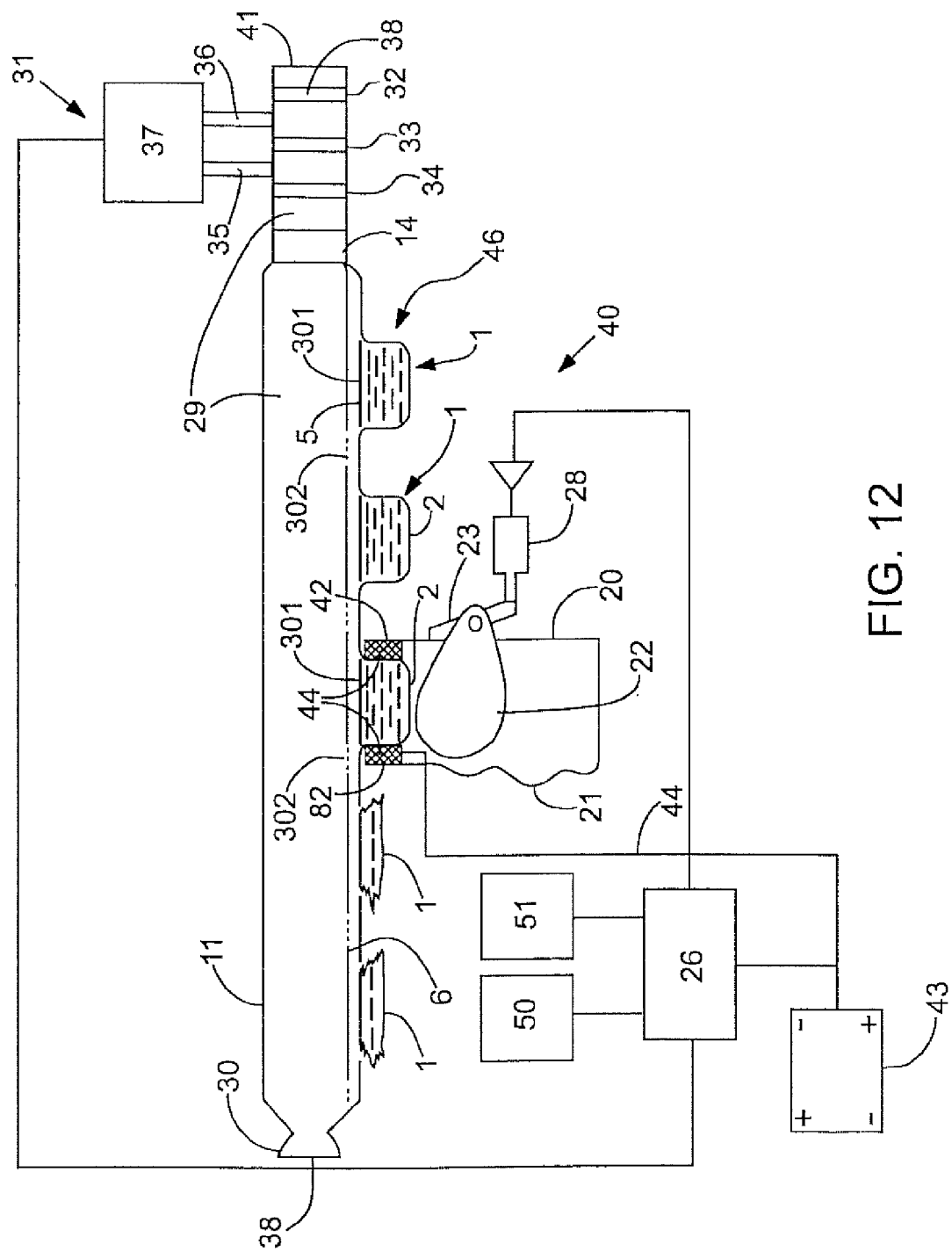
FIG. 12 is a cross-sectional view of an aerosol delivery device of the invention.

The aerosol delivery devices of the invention can also comprise additional components such as, but not limited to, a monitor for analyzing a patient's inspiratory flow (e.g., a flow sensor 31 as shown in FIG. 12 having tubes 35 and 36 connected to a pressure transducer 37, which tubes 35 and 36 communicate with the flow path 29 and which pressure transducer is electrically connected to a microprocessor 26), a heating mechanism for adding energy to the air flow into which the aerosol particles are released (e.g., a heating mechanism 14 as shown in FIG. 12), means for measuring ambient temperature and humidity (e.g., a hygrometer 50 and thermometer 51 as shown in FIG. 12), screens to prevent undesirable particles in the environment from entering the flow path (e.g., screens 32, 33, and 34 as shown in FIG. 12), and/or other components that might enhance aerosol delivery and/or patient compliance with an aerosol delivery regimen. The device can also comprise components that provide or store information about a patient's aerosol delivery regimen and compliance with such, the types and amounts of drug delivered to a patient, and/or other information useful to the patient or attending physician. Devices suitable for aerosol delivery according to the invention (i.e., that can be adapted for use with a low resistance filter and nozzle as described herein) are described in U.S. Pat. No. 5,544,646, issued Aug. 13, 1996; U.S. Pat. No. 5,497,763, issued Mar. 12, 1996; U.S. Pat. No. 5,855,562; PCT published application WO 96/13292, published May 9, 1996; and PCT published application WO 9609846, published Apr. 4, 1996, each of which is incorporated herein by reference to describe and disclose such aerosol delivery devices.

Aerosolization as described herein can be carried out with a device that obtains power from a plug-in source; however, the device is preferably a self-contained, portable device that is battery powered. For example, the methodology of the invention can be carried out using a portable, hand-held, battery-powered device which uses a microprocessor (e.g, as the means for recording a characterization of the inspiratory profile) as per U.S. Pat. Nos. 5,404,871; 5,450,336; and 5,906,202, incorporated herein by reference. The microprocessor is programmed using the criteria described herein using the device, dosage units, and system disclosed in U.S. Pat. Nos. 5,709,202; 5,497,763; 5,544,646; and 5,823,178, with modifications as described herein. Alternatively, the methodology of the invention can be carried out using a mechanical (nonelectronic) device. Those skilled in the art would recognize that various components can be mechanically set to actuate at a given inspiratory flow rate and at a given volume (e.g., a spinnable flywheel which rotates a given amount per a given volume).

Figure 13:
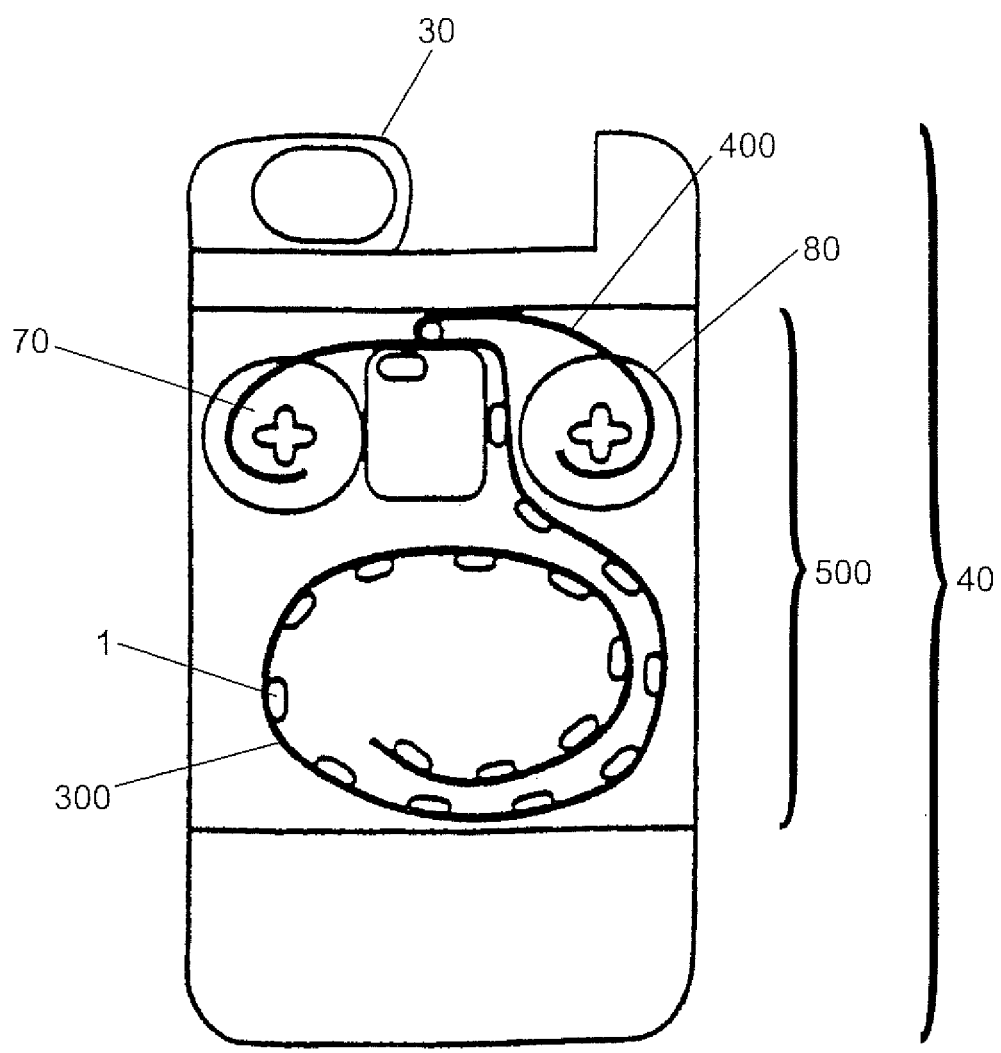
FIG. 13 is a cross-sectional view of an aerosol delivery device of the invention loaded with a cassette.

An exemplary device 40 of the invention is shown in FIG. 12. The device 40 is a hand held, self-contained, portable, breath-actuated inhaler device 40 having a holder 20 with cylindrical side walls and a hand grip 21. The holder 20 is "loaded," i.e., connected to a container 1 that includes dosage units having liquid, flowable formulations of pharmaceutically active drug or diagnostic agent therein. A plurality of containers 1 (2 or more) are preferably linked together to form a package 46. FIG. 13 is a cross-sectional view of a cassette 500 loaded into a delivery device 40. The disposable package 46 is folded or wound into the cassette 500 in a manner which makes it possible to move the individual containers 1 into a formulation release position within the device 40. While the containers 1 are moved into position the cover 400 is removed. Although it is possible to rewind any used portion of the package on a sprocket 70 and rewind the used cover 400 on a sprocket 85 or randomly fold it into a compartment, it is also possible to dispense the used portion outside of the cassette 500 and device 40 and immediately dispose of such.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entirety.

EXAMPLES

Example 1

Generation of Stepped Pores in Reduced-Pressure Aerosolization Nozzles

Nozzles were prepared from thin-film polyimide (25 μm, KAPTON™ Type 100H, DuPont de Nemours Co., Inc.) using an excimer laser. Before drilling the pores, the polyimide film was laminated to an aluminum-polyethylene composite lid layer through comprising one or more die-cut holes, each approximately 6 mm×1.5 mm. The laminate was held by a vacuum platen to a three axis stage.

A 7×48 array of holes in an area of 2.8 mm×0.5 mm was ablated in the polyimide using 5× projection lens. A mask containing an array of transparent areas of 125 μm in diameter was used to generate pores having an entrance diameter of 25 μm. About 40 pulses of an excimer laser at 630 mJ/cm$^2$ were used to ablate a first step partially through the membrane, to a depth of about 15 μm, thereby forming the first pore step. Then the mask was moved to a different position having UV transparent areas of 20 μm to generate a second pore step in the pores, the second step having an entrance aperture of about 4 μm and an exit aperture of about 1.25 microns using about 65 pulses of the same laser.

Figure 3:
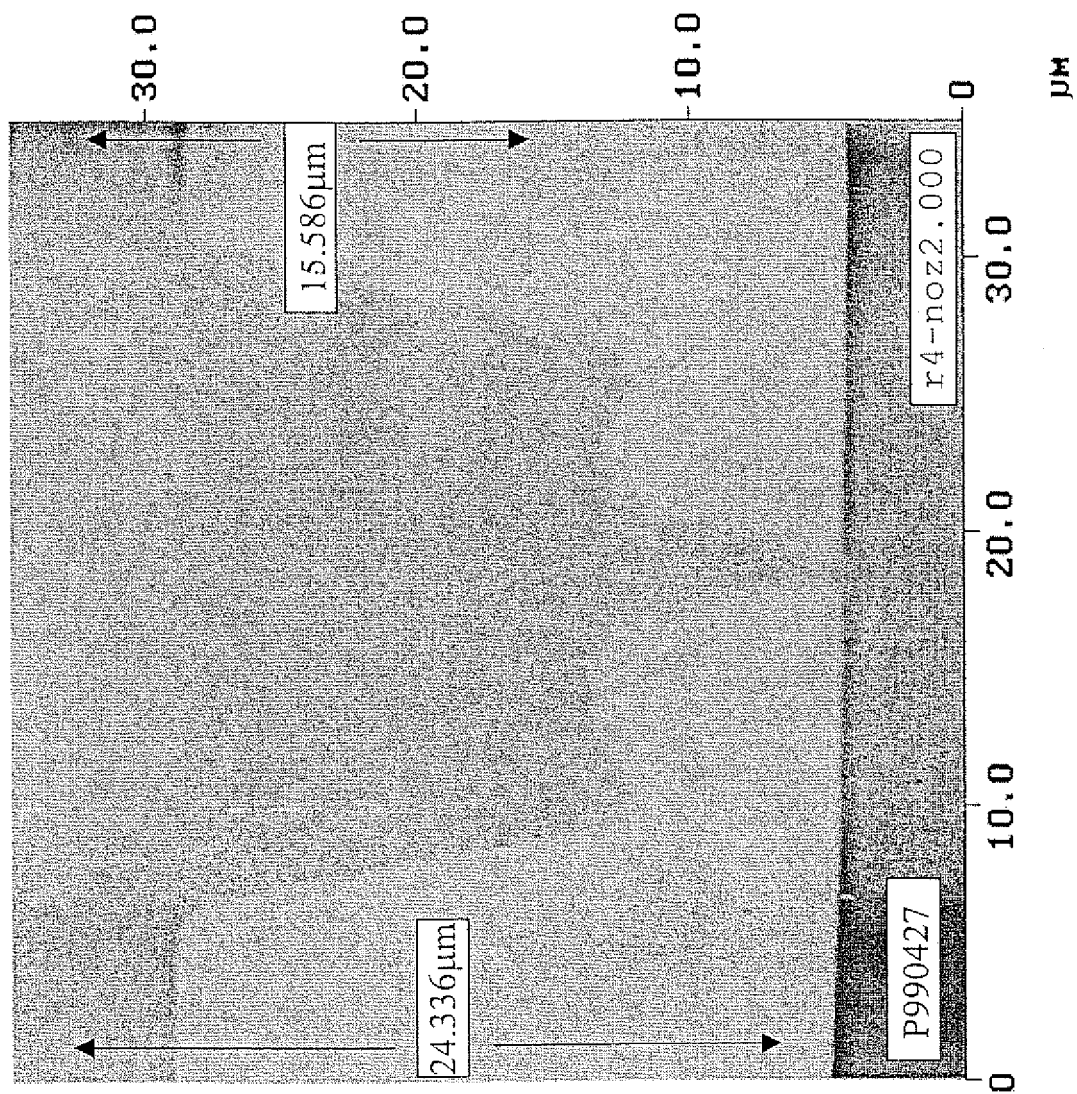
FIG. 3 is a scanning electron micrograph of a two-step pore formed via multi-step laser ablation. Dimensions are given in micrometers.

A scanning electron micrograph image of an example of a two-step pore is shown in FIG. 3.

Example 2

Dosage Fours and Blister Packs

A polyimide-aluminum/polyethylene laminate was made, and a 7×48 array of holes in a 2.8 mm×0.5 mm of the polyimide was formed as described in Example 1. A section of laminate comprising one 7×48 array of holes is a single nozzle. To make a single dosage form, an Aclam blister layer filled with a formulation was heat-sealed to a single nozzle. A single dosage form is shown in FIG. 6. A clamp was formed around the blister and nozzle area. Application of 200 to 400 psi of pressure to the dosage unit resulted in extrusion of the formulation from the blister, through the pores in the nozzle, whereby an aerosol was formed. The time from initial application of pressure to aerosol formation was 1.5 seconds.

To make a blister pack comprising multiple dosage forms, a polyimide layer was laminated to an aluminum/polyethylene layer as described in Example 1, where the aluminum/polyethylene composite lid layer comprised a regular array of die-cut holes, each about 6 mm×1.5 mm. Holes were drilled in the polyimide layer in each of the nozzle areas, as described in Example 1. An Aclam layer comprising a plurality of blisters filled with liquid formulation was heat-sealed onto the laminate, such that each nozzle area was juxtaposed to a formulation-filled blister, as shown in FIGS. 7 and 8.

Example 3

Formation of Pores Using Grayscale Process

Figure 4:
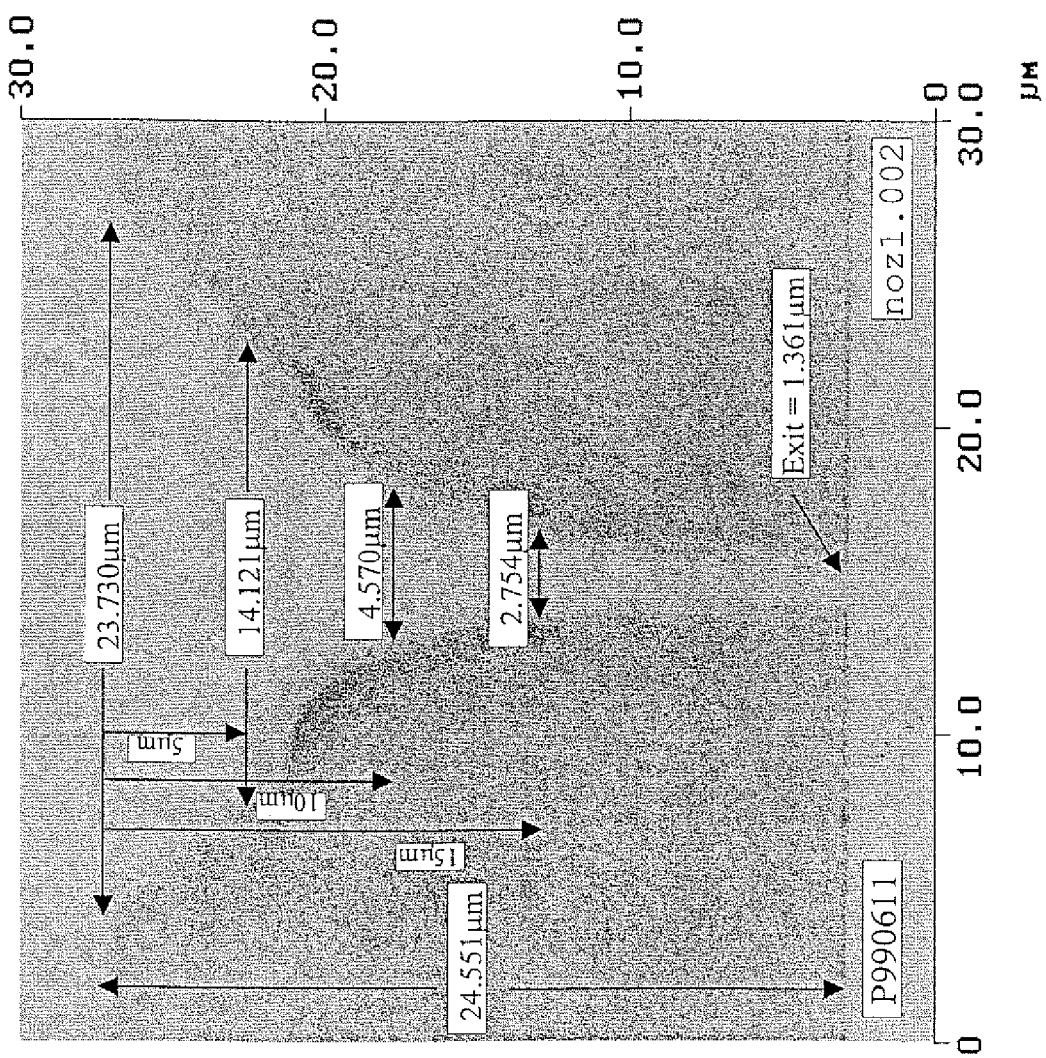
FIG. 4 is a scanning electron micrograph of a pore formed using a grayscale process. Dimensions are given in micrometers.

A mask comprising a first, inner circular area which allowed 100% transmission of energy, a second, circular area surrounding and concentric with the first area which comprised a density of opaque dots such as to allow 50% transmission of energy, was used to generate pores in a 25 µm thick KAPTON™ film. The first circular area had a diameter of 6 µm, while the second area had a diameter of 25 µm. An excimer laser as described in Example 1 was used. 120 pulses of an excimer laser at an energy density of 570 mJ/cm$^2$ was directed onto the mask and through the film until pores were formed. A cross-sectional image of a pore formed in this manner is depicted in FIG. 4.

Two types of Grayscale nozzles were made in this manner. Type I and Type II nozzles comprise pores having inner circle entrance diameters of 6 µm and 5 µm, respectively, as shown in Table 1.

TABLE 1

|  | Inner circle Diameter µm | Energy Density mJ/cm$^2$ | No. Pulses | Focus µm |
| --- | --- | --- | --- | --- |
| Type I | 6 | 570 | 120 | 0 |
| Type II | 5 | 660 | 120 | 0 |

When used in an aerosolization packet, as described in Example 2, grayscale nozzles generated aerosols having an average particle size of 2.5 µm, and an emitted dose of about 65% (i.e., the percentage of the formulation held in the container which was emitted). These parameters, i.e., average particle size and emitted dose, were the same as those obtained using a "standard" nozzle. A "standard" nozzle has pores with an entrance diameter of about 6 µm and an exit diameter of about 1 µm, as shown in FIG. 1, but otherwise is the same as the grayscale nozzle.

The Type I and Type II grayscale nozzles, as well as a standard nozzle, were analyzed for extrusion pressure required to generate an aerosol having average particle size of 2.5 µm, and an emitted dose of about 65%. The pressure required to generate such an aerosol using a standard nozzle is about 650 psi. A total of 70 individual packets comprising of Type I or Type II grayscale nozzles were analyzed. The average extrusion pressure required to generate an aerosol with the above-mentioned parameters was 297.14 psi for the Type I, and 358.45 psi for the Type II grayscale nozzle.

Example 4

Formulation of Pores by Dithering

Figure 5:
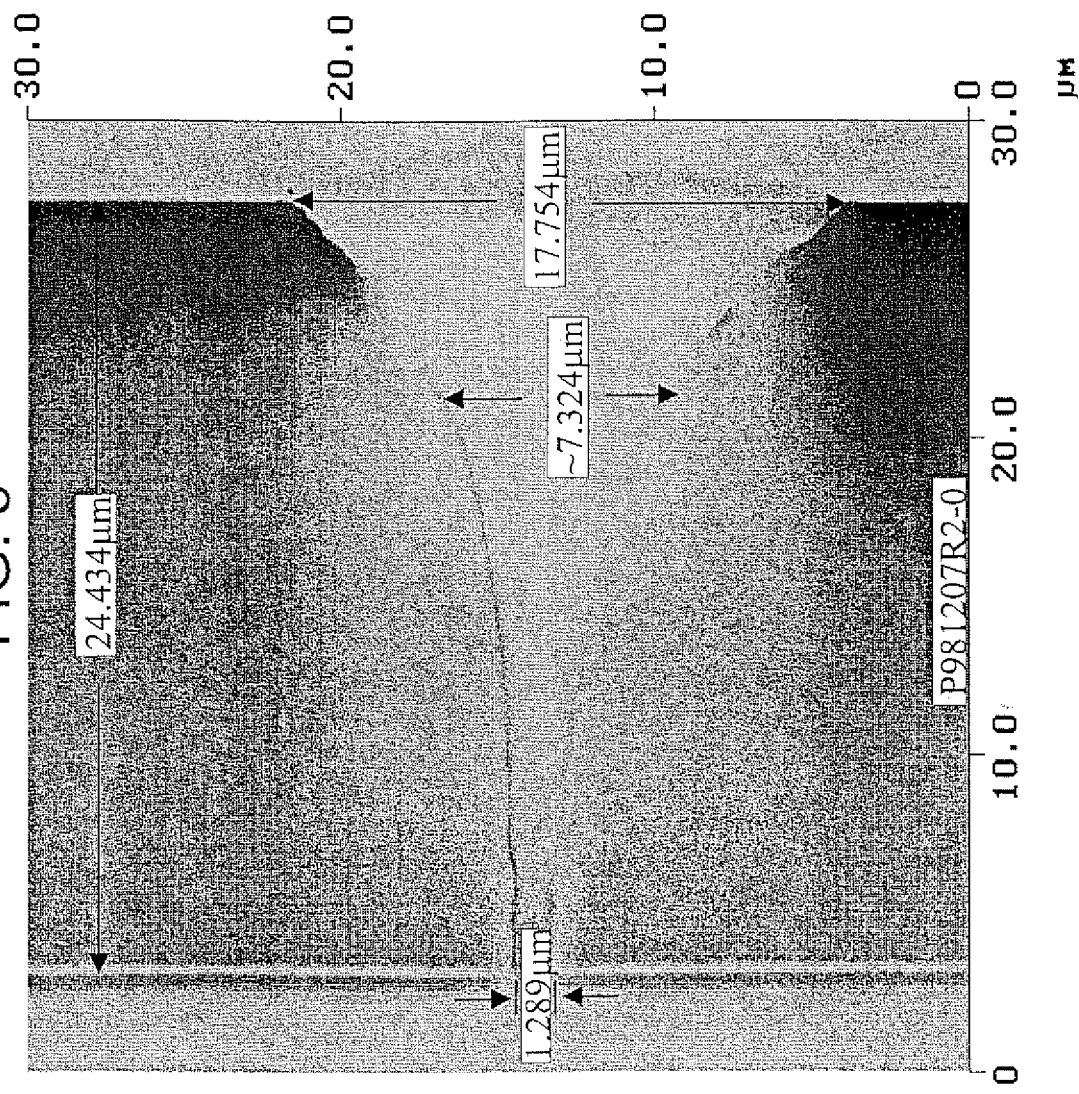
FIG. 5 is a scanning electron micrograph of a pore formed using a dithering process. Dimensions are given in micrometers.

A laser beam with an entrance aperture of 30 nm at the mask was displaced from the origin by 10 µm. The beam was rotated during the ablation process, thereby directing the laser to etch the membrane in a roughly circular pattern, through the thickness of the membrane, in a decreasing radius with each successive step for several steps to etch the polyimide membrane (25 µm thick), forming pores having a cross-sectional profile as shown in FIG. 5.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An aerosol delivery device, comprising
  a) a sheet, said sheet having a plurality of pores, wherein each of said pores has an entrance aperture size and an exit aperture size, and wherein the ratio of said entrance aperture size to said exit aperture size is at least about 10:1; and
  b) a container with a flowable liquid formulation, wherein said sheet has an entrance side to which said formulation is applied.

2. The device of claim 1, wherein the amount of liquid formulation in the container is from about 10 microliters to about 100 milliliters.

3. The device of claim 2, wherein the amount of liquid is from about 10 milliliters to about 90 milliliters.

4. The device of claim 2, wherein the amount of liquid is from about 20 microliters to about 100 microliters.

5. The device of claim 1, wherein the sheet is rigid.

6. The device of claim 1, wherein the sheet is a flexible membrane.

7. The device of claim 1, wherein the container is refillable.

8. The device of claim 1, wherein the container is disposable.

9. The device of claim 1, wherein the formulation is applied to the entrance side of the sheet by the application of a force to at least one wall of the container.

10. The device of claim 9, wherein the force leads to a pressure inside the container of less than about 725 psi.

11. The device of claim 1, wherein there is a low resistance filter positioned between the sheet and the container.

12. The device of claim 11, wherein the filter has a porosity such that the presence of the filter does not substantially increase the pressure required to generate an aerosol.

13. The device of claim 1, wherein the exit apertures of the pores are surrounded by elevated areas.

14. The device of claim 1, wherein the container includes an opening which leads to an open channel which channel includes a peelable seal which is peeled open upon the application of a force which is created by formulation being forced from the container.

15. A method of delivery of a drug to a patient, comprising:
   inhaling from the device of claim 1.

\* \* \* \* \*